US008889615B2

(12) United States Patent
Tomic-Canic et al.

(10) Patent No.: US 8,889,615 B2
(45) Date of Patent: Nov. 18, 2014

(54) METHODS FOR PROMOTING EPITHELIALIZATION AND HEALING OF CHRONIC WOUNDS

(75) Inventors: Marjana Tomic-Canic, Miami, FL (US); Harold Brem, Bronx, NY (US)

(73) Assignee: New York University, New York, NY (US)

( * ) Notice: Subject to any disclaimer, the term of this patent is extended or adjusted under 35 U.S.C. 154(b) by 14 days.

(21) Appl. No.: 13/519,551

(22) PCT Filed: Dec. 29, 2010

(86) PCT No.: PCT/US2010/062361
§ 371 (c)(1),
(2), (4) Date: Jun. 27, 2012

(87) PCT Pub. No.: WO2011/082231
PCT Pub. Date: Jul. 7, 2011

(65) Prior Publication Data
US 2012/0289463 A1    Nov. 15, 2012

Related U.S. Application Data

(60) Provisional application No. 61/291,669, filed on Dec. 31, 2009.

(51) Int. Cl.
| | |
|---|---|
| *A01N 61/00* | (2006.01) |
| *A61K 31/00* | (2006.01) |
| *A61K 38/00* | (2006.01) |
| *C07K 14/47* | (2006.01) |
| *A61P 17/00* | (2006.01) |
| *A61K 31/4741* | (2006.01) |
| *A61K 31/136* | (2006.01) |
| *A61K 31/366* | (2006.01) |
| *A61K 45/06* | (2006.01) |

(52) U.S. Cl.
CPC ............ *A61K 31/00* (2013.01); *A61K 31/4741* (2013.01); *A61K 31/136* (2013.01); *A61K 31/366* (2013.01); *A61K 45/06* (2013.01)
USPC ................................ 514/1; 514/7.5; 514/18.6

(58) Field of Classification Search
None
See application file for complete search history.

(56) References Cited

U.S. PATENT DOCUMENTS

| | | | |
|---|---|---|---|
| 5,624,824 | A | 4/1997 | Yuan |
| 5,705,629 | A | 1/1998 | Bhongle |
| 5,902,880 | A | 5/1999 | Thompson |
| 6,146,886 | A | 11/2000 | Thompson |
| 6,610,478 | B1 | 8/2003 | Takle |

FOREIGN PATENT DOCUMENTS

| | | |
|---|---|---|
| WO | 9322434 | 11/1993 |
| WO | 9524489 | 9/1995 |
| WO | 2009016629 | 5/2009 |

OTHER PUBLICATIONS http://www.complexwoundhealing.org/research/wound-healing-regenerative-medicine-research.html—accessed on the internet Jan. 16, 2013.*
Numakawa T., et al., PNAS 106(2):647-652, Jan. 13, 2009.*
Stojadinovic O, et al. Wound Repair and Regeneration, 12(2):A36, Apr. 2004 (Fourteenth Annual Meeting and Exhibition of the Wound Healing Society).*
Liu C, et al. Cell, 108:837-847, Mar. 22, 2002.*
Arnold and Watt, "c-Myc activation in transgenic mouse epidermis results in mobilization of stem cells and differentiation of their progeny" , Curr. Biol., 11:558-68 (2001).
Atschul, at al., "Basic local alignment search tool" , J. Molec. Biol., 215: 403-10 (1990).
Bayer, et al., "On the mode of liposome-cell interactions. Biotin-conjugated lipids as ultrastructural probes" , Biochim. Biophys. Acta. 550:464-73 (1979).
Beer, at al., "Glucocorticoid-regulated gene expression during cutaneous wound repair" , Vitam. Horm., 59:217-39 (2000).
Biro, et al., "Inhibitory effects of antisense oligodeoxynucleotides targeting c-myc mRNA on smooth muscle cell proliferation and migration" , PNAS, 90:654-8 (1993).
Bleasdale, et al., "Selective inhibition of receptor-coupled phospholipase C-dependent processes in human platelets and polymorphonuclear neutrophils" , J. Pharmacol. Exp. Thor., 255:756-68 (1990).
Brem, at al., "Healing of elderly patients with diabetic foot ulcers, venous stasis ulcers, and pressure ulcers" , Surg. Tech Intl, 161-7 (2003).
Brennecke, et al., "Discrete small RNA-generating loci as master regulators of transposon activity in *Drosophila*" , Cell, 128(6):1089-103 (2007).
Croxtall, et al., "Glucocorticoids act within minutes to inhibit recruitment of signalling factors to activated EGF receptors through a receptor-dependent, transcription-independent mechanism" , Br. J. Pharmacol., 130:289-98 (2000).

(Continued)

*Primary Examiner* — Robert Landsman
(74) *Attorney, Agent, or Firm* — Pabst Patent Group LLP

(57) ABSTRACT

Compositions for antagonizing phosphorylation and subsequent degradation of glycogen synthase kinase 3 beta (GSK3β) in epidermal cells are disclosed. GSK3β phosphorylation antagonists include molecules that function to inhibit or reduce the binding activity or enzymatic activity of an upstream signaling molecule leading to GSK3β phosphorylation, or by downregulating the expression of one or more upstream signaling molecules involved in regulating GSK3β phosphorylation. Methods of using the GSK3β phosphorylation antagonists to inhibit or reduce the phosphorylation and degradation of GSK3β in epidermal cells are provided. The methods are useful to promote epithelialization and closure of wounds, such as chronic non-healing wounds.

19 Claims, 2 Drawing Sheets

(56) References Cited

OTHER PUBLICATIONS

De Bosscher, et al., "Mechanisms of anti-inflammatory action and of immunosuppression by glucocorticoids: negative interference of activated glucocorticoid receptor with transcription factors", J. Neuroimmunol., 109:16-22 (2000).

Debs, et al, "Regulation of gene expression in vivo by liposome-mediated delivery of a purified transcription factor", J. Biol. Chem., 265:10189-192 (1990).

Ehrlich and Hunt, "Effects of cortisone and vitamin A on wound healing", Ann. Surg., 167:324-28 (1968).

Gandarillas and Watt, "c-Myc promotes differentiation of human epidermal stem cells", Genes Dev., 11:2869-82 (1997).

Guan, et al., "Glucocorticolds control beta-catenin protein expression and localization through distinct pathways that can be uncoupled by disruption of signaling events required for tight junction formation in rat mammary epithelial tumor cells", Mol. Endocrinol., 18:214-27 (2004).

Lee, et al., "From an enhanceosome to a repressosome: molecular antagonism between glucocorticoids and EGF leads to inhibition of wound healing", J. Mol. Biol., 345:1083-97 (2005).

Lee, "Comprehensive transcriptional profiling of human epidermis, reconstituted epidermal equivalents, and cultured keratinocytes using DNA microarray chips", Methods Mol. Biol. 585:193-23 (2009).

Leis, et al., "Glucocorticoid Receptor Counteracts Tumorigenic Activity of Akt in Skin through Interference with the Phosphatidylinositol 3-Kinase Signaling Pathway", Mol. Endocrinol., 18:303-11 (2004).

Lowenberg, et al., "Rapid immunosuppressive effects of glucocorticoids mediated through Lck and Fyn", Blood, 106:1703-10 (2005).

March, et al., "Role of the extracellular matrix in the degradation of connective tissue", Arch. Dermatol, Res., 287:107-14 (1994).

Masckauchan, "Wnt5a signaling induces proliferation and survival of endothelial cells in vitro and expression of MMP-1 and Tie-2", Mol. Biol. Cell, 17 (12):5163-72 (2006).

Morasso, et al., "Epidermal stem cells: the cradle of epidermal determination, differentiation and wound healing", Biol. Cell, 97:173-183 (2005).

Qi, et al., "Rapid activation of JNK and p38 by glucocorticoids in primary cultured hippocampal cells", J. Neurosci. Res., 80:510-7 (2005).

Radoja, "Novel mechanism of steroid action in skin through glucocorticoid receptor monomers", Mol. Cell. Biol., 20:4328-39 (2000).

Reed and Clark, "Cutaneous tissue repair: practical implications of current knowledge. II", J. Am. Acad. Dermatol., 13:919-41 (1985).

Schacke, et al., "Mechanisms involved in the side effects of glucocorticoids", Pharmacol. Ther., 96:23-43 (2002).

Scheinman, et al., "Role of transcriptional activation of I kappa B alpha in mediation of immunosuppression by glucocorticoids", Science, 270:283-6 (1995).

Schumacher and Chen, "Injectable corticosteroids in treatment of arthritis of the knee", Am. J Med., 118:1208-14 (2005).

Shimm and Smart, "Lithium stabilizes the CCAAT/enhancer-binding protein alpha (C/EBPalpha) through a glycogen synthase kinase 3 (GSK3)-independent pathway involving direct inhibition of proteasomal activity.", J. Biol. Chem., 278:19674-81 (2003).

Smith and Frankel, "Glucocorticoids inhibit the transcriptional activity of LEF/TCF in differentiating osteoblasts in a glycogen synthase kinase-3beta-dependent and -independent manner", J. Biol. Chem., 280:2388-94 (2005).

Smith, et al., "Receptor-coupled signal transduction in human polymorphonuclear neutrophils: effects of a novel Inhibitor of phospholipase C-dependent processes on cell responsiveness", J. Pharmacol. Exp. Ther., 253:688 (1990).

Sponsel, et al., "Adenine nucleotide and protein Kinase C regulation of rental tubular epithelial cell wound healing", Kidney Intl., 48(1):85-92 (1995).

Stojadinovic, et al., "Molecular pathogenesis of chronic wounds: the role of beta-catenin and c-myc in the inhibition of epithelialization and wound healing", Am. J. Pathol., 167(1):59-69 (2005).

Stojadinovic, et al., "Deregulation of keratinocyte differentiation and activation: a hallmark of venous ulcers", JCMM, 12(6B):2675-90 (2008).

Stojadinovic, "Novel genomic effects of glucocorticoids in epidermal keratinocytes: inhibition of apoptosis, interferon-gamma pathway, and wound healing along with promotion of terminal differentiation", Jour. Biol, Chem.,282(6):4021-34 (2007).

Tcacencu, "Mifepristone (RU-486) impairs post-surgical wound healing of the larynx", Med, Sci. Monitor, 8(10):BR397-400 (2002).

Trieu, et al., "Weekly cyclophosphamide and alternate-day prednisone: an effective, convenient, and well-tolerated oral treatment for relapsed multiple myeloma after autologous stem cell transplantation", Mayo. Clin. Proc., 80:1578-82 (2005).

Waikel, et al., "Deregulated expression of c-Myc depletes epidermal stem cells", Nat. Genet., 28:165-8 (2001).

Zavadil, et al., Integration of TGF-beta/Smad and Jagged1/Notch signalling in epithelial-to-mesenchymal transition\, EMBO J., 23:1155-65 (2004).

Zettl, et al., "Glucocorticoid-induced formation of tight junctions in mouse mammary epithelial cells in vitro", PNAS, 89:9069-73 (1992).

Zhang, at al., "The glucocorticoid agonist activities of mifepristone (RU486) and progesterone are dependent on glucocorticoid receptor levels but not on EC50 values", Steroids, 72:600-8 (2007).

Zhou, et al., "The human glucocorticoid receptor: one gene, multiple proteins and diverse responses", Steroids, 70:407-17 (2005).

* cited by examiner

METHODS FOR PROMOTING EPITHELIALIZATION AND HEALING OF CHRONIC WOUNDS

CROSS REFERENCE TO RELATED APPLICATIONS

This application is a filing under 35 U.S.C. §371 of PCT/US2010/062361 filed with the Patent Cooperation Treaty on Dec. 29, 2010, which claims priority to and benefit of U.S. Provisional Application No. 61/291,669, filed on Dec. 31, 2009, the contents of each being hereby incorporated by reference in their entirety.

STATEMENT REGARDING FEDERALLY SPONSORED RESEARCH OR DEVELOPMENT

This invention was made with government support awarded by the National Institutes of Health under Grant Numbers AR45974 and NR08029 to Marjana Tomic-Canie and DK59424 and LM008443 to Harold Brem. The United States government has certain rights in this invention.

FIELD OF THE INVENTION

The present disclosure is generally related to compositions and methods for promoting epithelialization and wound healing.

BACKGROUND OF THE INVENTION

It is estimated that each year greater than 7 million people develop chronic, non-healing wounds in the United States. A majority of chronic wounds fall into three categories: pressure, venous and diabetic ulcers. The incidence is 0.78% of the population and the prevalence ranges from 0.18 to 0.32%. As the population ages, the number of chronic wounds is expected to rise (Crovetti, et al., *Transfus. Apher. Sci.*, 30:145-51 (2004); Moreo, *Case Manager*, 16:62-3, 67 (2005); Supp, et al., *Clin. Dermatol.*, 23:403-12 (2005); Mutoe, *Am. J. Surg.*, 187:65S-70S (2004)). The National Pressure Ulcer Advisory Panel reports wide ranges of prevalence among patients in the United States. World-wide, in 2005, diabetes affected approximately 171 million people, including 20.8 million Americans, (7% of the population) according to 2005 NIH data. By 2030, these numbers are projected to double (Wild, et al., *Diabetes Care*, 27:1047-53 (2004)). Chronic wounds precede 84% of all diabetes-related lower-leg amputations (Reiber, et al., *Diabetes Care*, 22:157-62 (1999)). Therefore, understanding the pathogenesis and the ability to accelerate healing of these ulcers would have a major public health impact.

Skin integrity and its normal function depend on the ability of keratinocytes to maintain the barrier. In healthy epidermis, keratinocytes slowly proliferate in the basal layer and differentiate in the suprabasal layers. Basal keratinocytes are mitotically active. Once they leave the basal cell compartment they change their phenotype to differentiating. During the process of differentiation, they stop dividing, change the keratin production from K5/K14 to K1/K10, and begin to produce a number of insoluble proteins. At the end of the process they lose their nuclei and cross link their proteins giving rise to a cornified layer, forming a barrier. However, keratinocytes must respond very quickly to injury. In the case of injury, keratinocytes must inform each other that the bather has been broken and must be repaired (Freedberg, et al., *J. Invest. Dermatol.*, 116:633-40 (2001); Tomic-Canic, et al., *The epidermis in wound healing*, Eds. Rovee and Maibach, CRC Press LLC, pps. 25-7 (2004); Morasses and Tomic-Canic, *Biol. Cell*, 97:173-83 (2005); Tomic-Canic, *Wounds*, 17:s3-6 (2005)). In response, they change their phenotype to activated (wound healing), alert the host defense mechanisms that the barrier has been broken and that pathogens may be intruding. As a response to their own signals, keratinocytes start migrating and proliferating. Epithelialization is an important component of wound healing, often used as its defining parameter (Brem, et al., *Surgical Technology International*, 161-7 (2003)). This process is governed by extracellular signals such as pro-inflammatory cytokines and growth factors (Freedberg, et al., *J. Invest. Dermatol.*, 116:633-40 (2001); Tomic-Canic, et al., *J. Dermatol. Sci.*, 17:167-81 (1998); Kupper, *J. Invest. Dermatol.*, 94:146S-150S (1990); Parks, *Wound Repair Regen.*, 7:423-32 (1999); Mast, et al., *Wound Repair Regen.*, 4:411-20 (1996)). To close the gap, keratinocytes must first "let go of their anchor", i.e., loosen their adhesion to each other and to the basal lamina, and they must obtain the flexibility and ability to "grasp, hold and crawl" over the matrix freshly deposited by dermal fibroblasts. This requires rearrangement of the integrin receptors, reassembly of the associated actin cytoskeleton and the keratin filament network. Once the wound surface is covered by a keratinocyte monolayer, the proliferation signals cease and a new stratification process begins again.

Epidermal morphology of chronic ulcers differs from normal epithelial tissue and suggests that keratinocytes do not successfully complete either of the two possible pathways: activation or differentiation (Stojadinovic, et al., *Am. J. Pathol.*, 167:59-69 (2005)). Instead, keratinocytes are caught in a 'loop' of trying, but not succeeding, to achieve either of the two processes. Non-healing keratinocytes of the chronic wound are marked by activation of glucocorticoid receptor (GR), induction of c-myc and nuclear presence of β-catenin, and de-regulation of EGF leading to increased proliferation and inhibition of migration (Brem, et al., *Mol. Med,* 13:30-9 (2007); Stojadinovic, et al., *Am. J. Pathol.*, 167:59-69 (2005); Vukelic, et al., *Wound Healing Society Meeting; Tampa, Wound Repair and Regen.*, A34 (2007)).

Glucocorticoids (GCs) act through glucocorticoid receptor(s) (GR) that may be active in all three cellular compartments: nuclear, cytoplasmic and membranous (Lee and Tomic-Canic, *Molecular Mechanisms of Action of Steroid Hormone Receptors*, Ed. Krstic, Research Signpost, pps. 1-25 (2002); Yudt, et al., *Mol. Endocrinol.*, 15:1093-1103 (2001); Watson, et al., *EMBO Rep.*, 6:116-9 (2005)). In addition to operating as a transcription factor directly binding promoter elements (genomic effect), GCs also interact with and affect the activity of a variety of transcription factors, thus affecting transcriptional potency of many signaling pathways, such as TNFα, IFN, EGF, etc (non-genomic effects) (Zhou, et al., *Steroids*, 70:407-17 (2005)). Therefore, the complexity of GCs action resides in multiple signaling routes that not always require transcriptional regulation. The genomic mechanism consists of several important interactions. GR binds to specific sequences in targeted promoters (response elements, GRE) (So, et al., *PLoS Genet.*, 3:e94 (2007); Schoneveld, et al., *Biochim. Biophys. Acta*, 1680: 114-28 (2004); Kumar and Thompson, *J. Steroid Biochem. Mol. Biol.*, 94:383-94 (2005)). These sequences may mediate either activation (positive, GRE) or repression (negative, nGRE). Further, GR interacts with other transcription factors (AP-1, NF-kB) (De Bosscher, et al., *Mol. Endocrinol.*, 15:219-27 (2001); Herrlich, *Oncogene*, 20:2465-75 (2001); Okabe, et al., *Nippon Rinsho,* 63:1654-59 (2005); Smoak, et al., *Mech. Ageing Dev.*, 125:697-706 (2004)) or co-activators (such as GRIP-1, SRC-1) that modify its transcriptional signal (Cho, et al., *Biochemistry*, 44:3547-61 (2005); Li, et al., *Mol. Cell Biol.*, 23:3763-73 (2003); Li, et al., *Mol. Endocrinol.*, 20:1025-34 (2006); Ding, et al., *Mol. Endocrinol.*, 12:302-13 (1998)). Lastly, this DNA-GR-co-regulator complex further interacts with histone modifying enzymes (acetyl or methyl transferases) that participate in chromatin remodeling and either activate or repress transcription (Li, et al., *Mol. Cell Biol.*, 23:3763-73 (2003); Trotter, et al., *Mol. Cell. Endocrinol.*, 265-266:162-7 (2007); Kagoshima, et al., *Biochem. Soc. Trans.*, 31:60-5 (2003); Schurter, et al., *Biochemistry*, 40:5747-56 (2001); Koh, et al., *J. Biol. Chem.*, 277: 26031-5 (2002)).

In recent years, new aspects of GCs action have emerged. It was discovered that in addition to the effect that hormone bound GR has on transcriptional regulation, the receptor is capable of more rapid effects (non-genomic) such as changing the phosphorylation levels of other signaling molecules. The non-genomic effects are hormone dependant and mediated by the GR. Because they may affect signaling molecules, they may lead to transcriptional changes. Unlike in genomic effects, these transcriptional changes do not require direct interaction of GR with a promoter. For example, GCs can rapidly change the phosphorylation status of Lck/Fyn, interfere with $PI_3K$ and Akt, inhibit activity of LEF/TCF and may activate JNK, p38 and EGF signaling molecules (Croxtall, et al., *Br. J. Pharmacol.*, 130:289-98 (2000); Lowenberg, et al., *Blood*, 106:1703-10 (2005); Qi, et al., *J. Neurosci. Res.*, 80:510-7 (2005); Smith and Frankel, *J. Biol. Chem.*, 280: 2388-94 (2005); Leis, et al., *Mol. Endocrinol.*, 18:303-11 (2004)).

GCs are major therapeutic agents that significantly inhibit epithelialization and wound healing, affecting millions of surgical patients as they are utilized for the treatment of inflammatory bowel disease and organ transplant as well as in the treatment of multiple skin diseases (Baumann and Kerdel, *Fitzpatrick's Dermatology in General Medicine Vol. II*, Eds. Irwin, et al., McGraw-Hill, pps. 2713-7 (1999); Trieu, et al., *Mayo. Clin. Proc.*, 80:1578-82 (2005); Kesisoglou and Zimmermann, *Exp. Opin. Drug Del.*, 2:451-63 (2005); Lemann, et al., *Rev. Prat.*, 55:984-92 (2005); Schumacher and Chen, *Am. J Med.*, 118:1208-14 (2005)). GCs block inflammation, repress immune system activation, act as growth-inhibitory agents and inhibit wound healing (Ehrlich and Hunt, *Ann. Surg.*, 167:324-28 (1968); Beer, et al., *Vitam. Horm.*, 59:217-39 (2000); De Bosscher, et al., *J. Neuroimmunol.*, 109:16-22 (2000); Reed and Clark, *J. Am. Acad. Dermatol.*, 13:919-41 (1985)). Analyses of biopsies from patients suffering from chronic wounds revealed constitutive activation of GCs pathway and cortisol synthesis, suggesting that GCs play a role in the pathogenesis of chronic ulcers.

Most of the known GC effects are thought to be dermal (Schacke, et al., *Pharmacol. Ther.*, 96:23-43 (2002)), however, much less is known about the effects of GCs on epidermis. GCs affect epidermal biology in many different ways, including cell-cell interaction, ECM molecules, and as immunosuppressive agents (Zettl, et al., *Proc. Natl. Acad. Sci. USA*, 89:9069-73 (1992); Guller, et al., *Ann. NY Acad. Sci.*, 734: 132-42 (1994); Cronstein, et al., *Trans. Assoc. Am. Physicians*, 105:25-35 (1992); Scheinman, et al., *Science*, 270: 283-6 (1995)).

The molecular mechanisms involved in GCs-mediated inhibition of epithelialization are not well understood. A more complete understanding of the signaling pathways involved in GC-mediated inhibition of epithelialization would make it possible to design effective strategies to promote epithelialization and healing of chronic wounds.

Therefore, it is an object of the invention to provide compositions and methods to promote epithelialization and healing of chronic, non-healing wounds.

It is another object of the invention to provide compositions and methods to promote keratinocyte proliferation and migration at the leading edge of chronic, non-healing wounds.

It is yet another object of the invention to provide compositions and methods to inhibit or reduce induction of c-myc and nuclear presence of β-catenin in keratinocytes at the leading edge of chronic, non-healing wounds.

SUMMARY OF THE INVENTION

Compositions for antagonizing phosphorylation and subsequent degradation of glycogen synthase kinase 3 beta (GSK3β) in epidermal cells are disclosed. GSK3β phosphorylation antagonists include molecules that function to inhibit or reduce the binding activity or enzymatic activity of an upstream signaling molecule leading to GSK3β phosphorylation, or by downregulating the expression of one or more upstream signaling molecules involved in regulating GSK3β phosphorylation. GSK3β phosphorylation antagonists include molecules that inhibit or antagonize a product of an enzymatic activity of an upstream signaling molecule involved in regulating GSK3β phosphorylation. Upstream signaling molecules involved in GSK3β phosphorylation include any intracellular molecule that, when activated, directly or indirectly cause phosphorylation of GSK3β on serine 9, resulting in degradation of GSK3β.

In some embodiments, GSK3β phosphorylation antagonists include small molecules and peptides that inhibit or reduce phosphorylation of GSK3β on serine 9 in epidermal cells that results from binding of GCs to GRs. Suitable upstream signaling molecules involved in GSK3β phosphorylation include, but are not limited to, the components of the signaling pathways shown in FIG. 1. For example, GSK3β phosphorylation antagonists can include molecules that inhibit the enzymatic activity or enzymatic products of glucocorticoid receptor (GR), protein tyrosine kinase (PTK), G alpha q (Gαq), phospholipase C (PLC), or protein kinase C (PKC). In other embodiments, GSK3β phosphorylation antagonists include inhibitory nucleic acids, such as dsRNA, siRNA, shRNA, miRNA, piRNA, external guide sequences, ribozymes, and other short catalytic RNAs that inhibit expression of an mRNA that encodes an upstream signaling molecules involved in GSK3β phosphorylation at the transcriptional or translational level.

Methods of using the GSK3β phosphorylation antagonists to inhibit or reduce the phosphorylation and degradation of GSK3β in chronic non-healing wounds are provided. In one embodiment, the GSK3β phosphorylation antagonists are administered to an individual in an effective amount to promote wound healing. Wounds that may be treated include chronic, non-healing wounds, such as diabetic ulcers, arterial ulcer, venous ulcers, pressure ulcers and burns. In another embodiment, the GSK3β phosphorylation antagonists are used to promote healing of acute wounds, such as those caused by acute injury or surgery. The wound to be treated may be in any epithelial tissue, including skin, mouth tissue, gingival and corneal epithelium.

The GSK3β phosphorylation antagonists can be topically or subcutaneously administered at or adjacent to the site of a wound to be treated. They may be formulated into sustained release formulations and may be incorporated into wound dressings or wound inserts. The GSK3β phosphorylation antagonists can be used in combination with other therapies for treating wounds, including, but not limited to, anti-microbial agents, pain relievers, anti-inflammatory agents and growth factors.

DETAILED DESCRIPTION OF THE INVENTION

I. Pharmaceutical Compositions

Figure 1:
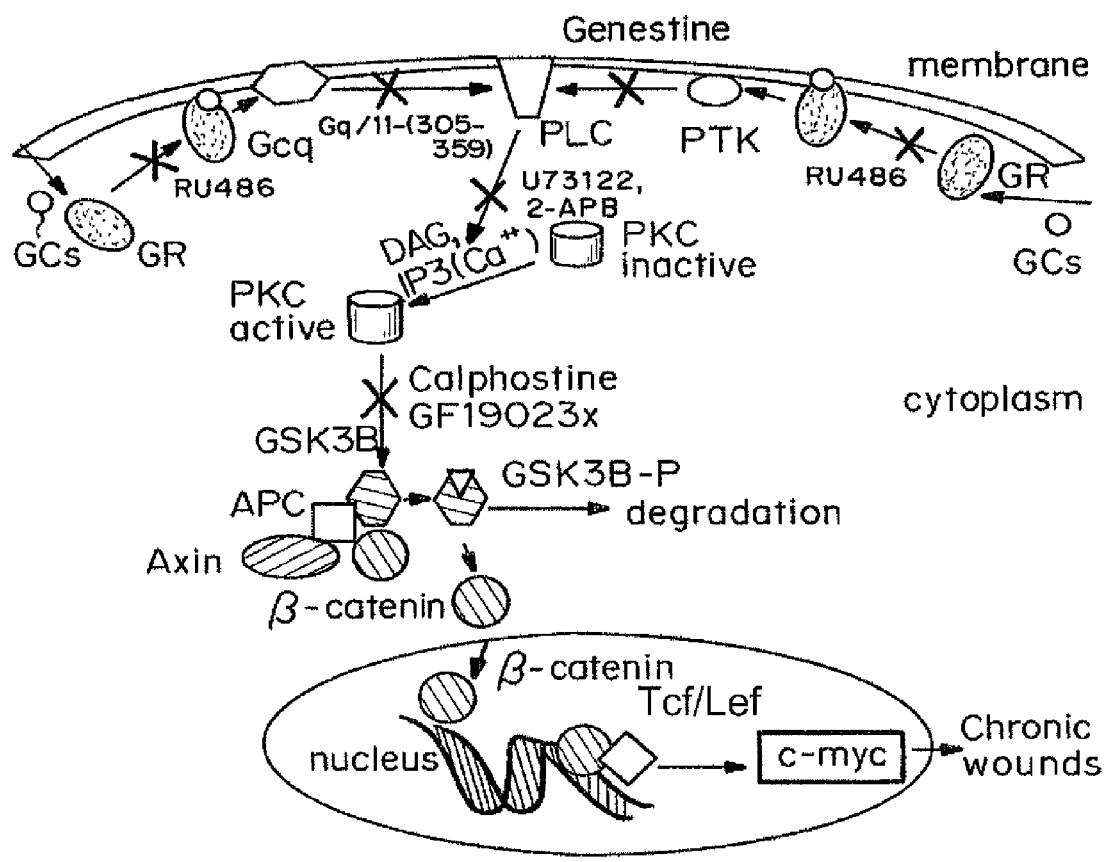
FIG. 1 is a schematic showing intracellular signaling pathways that are activated by glucocorticoids (GCs), leading to phosphorylation and degradation of GSK3β, and ultimately to the development of chronic wounds. Exemplary inhibitors for steps in this pathway are also shown.

A. Signaling Pathways Leading to β-catenin Nuclearization and Induction of c-myc As discussed above, keratinocytes at the leading edge of chronic, non-healing wounds are characterized by activation of the glucocorticoid receptor (GR), and nuclear presence of β-catenin. Among the downstream targets of the β-catenin transcriptional pathway is the oncogene, c-myc (He, at al., *Science*, 281:1509-12 (1998)). Activation of c-myc affects epidermal biology directly relevant to wound healing. Deregulation of c-myc depletes epidermal stem cells, disabling stem cells to react to injury (Waikel, et al., *Nat. Genet.*, 28:165-8 (2001); Arnold and Watt, *Curr. Biol.*, 11:558-68 (2001); Biro, et al., *Proc. Natl. Acad. Sci. USA*, 90:654-8 (1993); Gandarillas and Watt, *Genes Dev.*, 11:2869-82 (1997)). Targeted overexpression of c-myc in basal keratinocytes leads to impairment of keratinocyte migration and inhibition of wound healing (Waikel, et al., *Nat. Genet.*, 28:165-8 (2001)).

1. The Canonical Wnt/β-catenin Signaling Pathway

Wnt/β-catenin signals have been implicated in the development of many tissues and organs, including brain, neural crest, limbs, placenta, retina, cartilage, kidney, and uterus (Alonso and Fuchs, *Genes Dev.*, 17:1189-1200 (2003)). In skin, the Wnt pathway plays an important role in cell fate determination during development (Morasso and Tomic-Canic, *Biol. Cell*, 97:173-83 (2005); Huelsken, et al., *Cell*, 105:533-45 (2001); Merrill, et al., *Genes Dev.*, 15:1688-1705 (2001); Niemann, et al., *Development*, 129:95-109 (2002); Lo Celso, et al., *Development*, 131:1787-99 (2004)).

A number of Wnts are expressed in skin, including Wnt 3, 3a, 4, 5a, 7a, 7b, 10a, 10b, 11 and 16 (Millar, et al., *Dev. Biol.*, 207:133-149 (1999); Reddy, et al., *Mech. Dev.*, 107:69-82 (2001)). In the absence of a Wnt signal, epithelial β-catenin is found in stable complexes with E-cadherin, participating in cell-cell adhesion through the formation of the adherens junctions (AJs) (Geiger and Ayalon, *Ann. Rev. Cell Biol.*, 8:307-32 (1992); Zhurinsky, et al., *J. Cell Sci.*, 113:3127-39 (2000); Jamora and Fuchs, *Nat. Cell Biol.*, 4:E101-8 (2002); Polakis, *Curr. Biol.*, 12:R499-R501 (2002)). Excess β-catenin not used in AJs is phosphorylated by a glycogen synthase kinase 3β (GSK3β) kinase complex and then targeted for proteosome-mediated degradation (Hecht and Kemler, *EMBO Rep.*, 1:24-8 (2000); Watt, *J. Dermatol. Sci.*, 28:173-80 (2002); Gordon and Nusse, *J. Biol. Chem.*, 281:22429-33 (2006); Nusse, *Nature*, 438:747-9 (2005)). In response to a canonical Wnt signal, however, the GSK3β kinase complex is inactivated and accumulated β-catenin interacts with additional partners, such as the Lef/Tcf proteins that can interact with various chromatin-remodeling factors (Povelones and Nusse, *Nat. Cell Biol.*, 4:E249-50 (2002); Zorn, et al., *Mol. Cell*, 4:487-98 (1999); Labbe, et al., *Proc. Natl. Acad. Sci. USA*, 97:8358-63 (2000); Nishita, et al., *Nature*, 403:781-5 (2000); Daniels and Weis, *Mol. Cell*, 10:573-84 (2002); Chen, et al., *J. Biol. Chem.*, 275:17894-9 (2000)). β-catenin is also known to bind nuclear receptors, such as retinoic acid receptor (RAR) and androgen receptor (AR) (Li, et al., *J. Biol. Chem.*, 279:4212-20 (2004); Easwaran, et al., *Curr. Biol.*, 9:1415-18 (1999)), thus indicating that β-catenin may act as a co-regulator of nuclear receptors.

2. β-catenin Signaling Pathways Activated by Glucocorticoids (GCs)

In addition to the canonical Wnt/β-catenin signaling pathway outlined above, GCs can cause accumulation and nuclearization of β-catenin. For example, the GC dexamethasone (DEX) has been shown to induce β-catenin on the protein and mRNA level, and almost completely inhibits β-catenin phosphorylation, causing trans-epithelial resistance of mammary tumor epithelial cells (Guan, et al., *Mol. Endocrinol.*, 18:214-27 (2004)). While previous studies such as these have established that GCs can cause nuclearization of β-catenin through non-genomic mechanisms, the signaling pathways connecting GCs to β-catenin nuclearization in keratinocytes and subsequent inhibition of epithelialization in chronic wounds were previously unknown.

The examples demonstrate that cross-talk between the GCs and β-catenin pathways leads to inhibition of keratinocyte migration and epithelialization, and plays a role in the etiology of chronic wounds. GCs, such as dexamethasone, were found to inhibit GSK3β on the protein and mRNA levels, whereas β-catenin levels were not affected. However, GCs caused nuclearization of the β-catenin in epidermis. Furthermore, GCs also induced expression of c-myc, a β-catenin downstream target, on mRNA and protein levels. In addition, activation of GR, nuclearization of β-catenin and induction of c-myc were found in the non-healing epidermis deriving from patients with chronic ulcers.

The examples establish that GC signaling pathways in keratinocytes converge to cause phosphorylation of GSK3β, which causes its degradation. Degradation of GSK3β prevents it from phosphorylating β-catenin and causing its degradation, thus leading to β-catenin accumulation and translocation to the nucleus where it functions to upregulate the expression of genes such as c-myc, resulting on the development of a chronic wound. A schematic of the signaling pathways initiated by GC binding to GRs in the epidermis of chronic wounds leading to phosphorylation of GSK3β, nuclearization of β-catenin, induction of c-myc, and inhibition of epithelialization is shown in FIG. 1. As shown in FIG. 1, the binding of GCs to the GR in keratinocytes results in the activation of protein tyrosine kinases (PTKs) and heterotrimeric Gαq proteins. Activated PTKs and Gαq proteins can then, in turn, activate the enzymatic activity of phospholipase C (PLC) to cleave phosphatidylinositol 4,5-bisphosphate ($PIP_2$) to form diacyl glycerol (DAG) and inositol 1,4,5-triphosphate ($IP_3$). DAG remains bound to the membrane, and $IP_3$ is released as a soluble molecule into the cytosol, where it binds to $IP_3$ receptors, in particular calcium channels in the endoplasmic reticulum (ER). This causes the cytosolic concentration of calcium to increase. Calcium released by the action of $IP_3$ and DAG together activate protein kinase C (PKC). Activated PKC, in turn, phosphorylates glycogen synthase kinase 3 beta (GSK3β) on serine 9, resulting in its degradation by the proteasome. In the absence of an upstream signal, GSK3β exists in a complex with axin, β-catenin and adenomatosis polyposis coli protein (APC). In this complex, GSK3β kinase activity is activated, causing it to posphorylate β-catenin. Phosphorylated β-catenin is degraded by the proteasome. Degradation of GSK3β by phosphorylation on serine 9 relieves the inhibitory phosphorylation of β-catenin, which allows β-catenin to acculmulate in the cytosol and translocate to the nucleus. In the nucleus, β-catenin can complex with transcription factors such as Lef/Tcf to induce transcription of genes including c-myc.

B. Antagonists of GSK3β Phosphorylation and Degradation

Pharmaceutical compositions useful to promote epithelialization and closure of chronic, non-healing wounds, containing antagonists of GSK3β phosphorylation and degradation are disclosed. Antagonists of GSK3β phosphorylation are also referred to herein as "GSK3β phosphorylation antagonists". In preferred embodiments, GSK3β phosphorylation antagonists inhibit or reduce phosphorylation of GSK3β on serine 9 in epidermal cells that results from binding of GCs to GRs. GSK3β phosphorylation antagonists include molecules that function to inhibit or reduce the binding activity or enzymatic activity of an upstream signaling molecule leading to GSK3β phosphorylation, or by downregulating the expression of one or more upstream signaling molecules involved in regulating GSK3β phosphorylation.

GSK3β phosphorylation antagonists also include molecules that inhibit or antagonize a product of an enzymatic activity of an upstream signaling molecule involved in regulating GSK3β phosphorylation. Upstream signaling molecules involved in GSK3β phosphorylation include any intracellular molecule that, when activated, directly or indirectly cause phosphorylation of GSK3β on serine 9, resulting in degradation of GSK3β. Suitable upstream signaling molecules involved in GSK3β phosphorylation include, but are not limited to, the components of the signaling pathways shown in FIG. 1. For example, GSK3β phosphorylation antagonists can include molecules that inhibit the enzymatic activity, enzymatic product, or expression of GR, PTKs, Gαq, PLC or PKC. Suitable GSK3β phosphorylation antagonists include small molecule antagonists, peptide/polypeptide antagonists and inhibitory nucleic acids.

1. Small Molecule and Peptide Antagonists

In some embodiments, GSK3β phosphorylation antagonists are small molecules or peptides that inhibit or reduce the enzymatic activity or product of one or more upstream signaling molecules involved in regulating GSK3β phosphorylation in epidermal cells. Suitable small molecule antagonists include organic, inorganic, organo-metallic, synthetic, semi-synthetic and naturally occurring small molecules. Small molecule antagonists encompass numerous chemical classes, though typically they are organic molecules, preferably small organic compounds having a molecular weight of more than 100 and less than about 2,500 daltons, more preferably between 100 and 2000, more preferably between about 100 and about 1250, more preferably between about 100 and about 1000, more preferably between about 100 and about 750, more preferably between about 200 and about 500 daltons. Small molecule antagonists comprise functional groups necessary for structural interaction with proteins, particularly hydrogen bonding, and typically include at least an amine, carbonyl, hydroxyl or carboxyl group, preferably at least two of the functional chemical groups. Small molecule antagonists often comprise cyclical carbon or heterocyclic structures and/or aromatic or polyaromatic structures substituted with one or more of the above functional groups. Small molecule antagonists are also found among biomolecules including peptides, saccharides, fatty acids, steroids, purines, pyrimidines, derivatives, structural analogs or combinations thereof.

a. Protein Kinase C (PKC)

In some embodiments, the GSK3β phosphorylation antagonists are small molecules or peptides that inhibit or reduce the enzymatic activity of kinases that directly phosphorylate GSK3β on serine 9. Such kinases that directly phosphorylate GSK3β on serine 9 are referred to herein as GSK3β kinases. In preferred embodiments, the GSK3β kinases include one or more isoforms of protein kinase C (PKC). The examples demonstrate that PKC inhibitors are able to block dexamethasone-induced phosphorylation and degradation of GSK3β. The examples also demonstrate that PKC inhibitors are able to block GC-mediated nuclearization of β-catenin, activation of LEF/TCF-mediated transcription, and induction of c-myc. Finally, the examples demonstrate that PKC inhibitors are able to rescue inhibition of epithelialization in wounded human skin induced by GCs.

PKC is a family of protein kinases, and at least eleven closely related PKC isozymes have been reported that differ in their structure, biochemical properties, tissue distribution, subcellular localization, and substrate specificity. They are classified as conventional (α, β1,β2, γ), novel (δ,ε, η, θ, μ), and atypical (ζ, λ) isozymes. Conventional PKC isozymes are $Ca^{2+}$-dependent, while novel and atypical isozymes do not require $Ca^{2+}$ for their activation. All PKC isozymes, with the exception of ζ and λ, are activated by DAG.

Many suitable PKC inhibitors are known in the art and are publicly available through a number of commercial sources. Suitable PKC inhibitors include, but are not limited to, bis-indolylmaleimide I (GF 109203X) (2-[1-(3-Dimethylaminopropyl)-1H-indol-3-yl]-3-(1H-indol-3-yl)-maleimide), bis-indolylmaleimide II (2-[1-[2-(1-Methylpyrrolidino)ethyl]-

1H-indol-3-yl]-3-(1H-indol-3-yl)maleimide), bisindolylmaleimide III (2-[1-(3-Aminopropyl)-1H-indol-3-yl]-3-(1H-indol-3-yl)maleimide), bisindolylmaleimide IV (2,3-bis(1H-Indol-3-yl)maleimide), bisindolylmaleimide V (Ro 31-6045) (2,3-bis(1H-Indol-3-yl)-N-methylmaleimide), cardiotoxin from *Naja nigricollis*, chelerythrin, dequalinium, ellagic acid (4,4',5,5',6,6'-Hexahydroxydiphenic Acid 2,6,2',6'-Dilactone), Go 6983 (2-[1-(3-Dimethylaminopropyl)-5-methoxyindol-3-yl]-3-(1H-indol-3-yl) maleimide), Go 7874, H-7 (1-(5-Isoquinolinesulfonyl)-2-methylpiperazine), Iso-H-7 (1-(5-Isoquinolinesulfonyl)-3-methylpiperazine), HBDDE (2,2',3,3',4,4'-Hexahydroxy-1,1'-biphenyl-6,6'-dimethanol Dimethyl Ether), Hispidin (6-(3,4-Dihydroxy-styrl)-4-hydroxy-2-pyrone), K-252a, K-252b, K-252c, Melittin (H-Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-NH$_2$), Non-glycosidic Indolocarbazole I, Phloretin (2',4',6'-Trihydroxy-3-p-hydroxyphenylpropiophenone), Piceatannol (trans-3,3',4,5'-Tetrahydroxystilbene), Polymyxin B Sulfate, Ro-31-7549 (2-[1-3(Aminopropypindol) indol-3-yl]-3(1-methyl-1H-indol-3-yl)maleimide), Ro-31-8220 (3-[1-[3-(Amidinothio)propyl-1H-indol-3-yl]-3-(1-methyl-1H-indol-3-yl)maleimide), Ro-31-8425 (2-[8-(Aminomethyl)-6,7,8,9-tetrahydropyrido[1,2-a]indol-3-yl]-3-(1-methyl-1H-indol-3-yl)maleimide), Ro-32-0432 (3-(8-((dimethylamino)methyl)-6,7,8,9-tetrahydropyrido[1,2-α] indol-10-yl)-4-(1-methyl-1H-indol-3-yl)-1H-pyrrole-2,5-dione), Rottlerin, Safingol (L-threo-Dihydrosphingosine), Sangivamycin (7-Deaza-7-carbamoyladenosine), Scytonemin, D-erythro-Sphingosine, Staurosporine, Tamoxifen, TER14687 ((±)-2-N,N-Dimethylaminomethyl-1-indanone), UCN-01 (7-Hydroxystaurosporine) and UCN-02 (7-epi-Hydroxystaurosporine). Many PKC inhibitors have differential specificity for PKC isozymes. In some embodiments, PKC inhibitors include inhibitors that have a specificity conventional (α, β1, β2, γ).

In one embodiment, the PKC inhibitor is claphostin C. Calphostin C is a cell permeable, highly specific inhibitor of protein kinase C ($IC_{50}$=50 nM) that interacts with the protein's regulatory domain by competing at the binding site of diacylglycerol and phorbol esters.

The molecular structure for calphostin C is shown below:

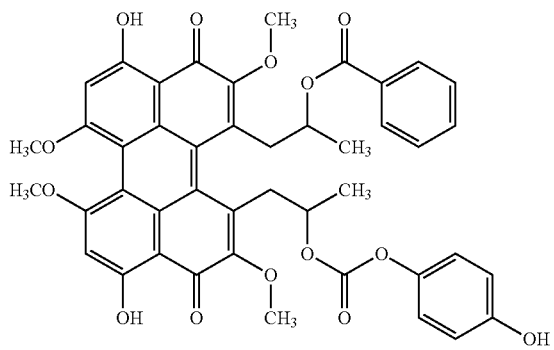 [SMILES: COc1c(CC(C)OC(=O)Oc2ccc(O)cc2)c2c3c(CC(C)OC(=O)c4ccccc4)c(OC)c(=O)c4c(O)cc(OC)c(c5c(OC)cc(O)c(c1=O)c52)c43]

In another embodiment, the PKC inhibitor is Go 6976 (12-(2-Cyanoethyl)-6,7,12,13-tetrahydro-13-methyl-5-oxo-5H-indolo(2,3-a)pyrrolo(3,4-c)-carbazole). Go 6976 is a cell-permeable inhibitor of protein kinase C (PKC; $IC_{50}$=7.9 nM for rat brain). This inhibitor electively inhibits $Ca^{2+}$-dependent PKC α-isozyme ($IC_{50}$=2.3 nM) and $PKC_{\beta I}$ ($IC_{50}$=6.2 nM). It does not affect the kinase activity of the $Ca^{2+}$-independent PKC d-, e-, and z-isozymes even at micromolar levels, but has been reported to inhibit $PKC_\mu$. at higher concentrations ($IC_{50}$=20 nM).

The molecular structure for Go 6976 is shown below:

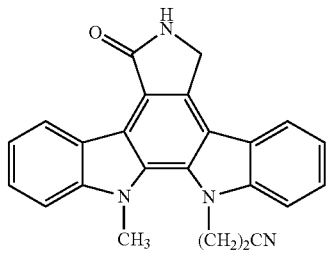

b. Phospholipase C (PLC)

In other embodiments, the GSK3β phosphorylation antagonists are small molecules or peptides that inhibit or reduce the enzymatic activity of PLC. The examples demonstrate that PLC inhibitors are able to block dexamethasone-induced phosphorylation and degradation of GSK3β. Many suitable PLC inhibitors are known in the art and are publicly available through a number of commercial sources.

Suitable PLC inhibitors include, but are not limited to, edelfosine (1-O-Octadecyl-2-O-methyl-rac-glycero-3-phosphorylcholine), neomycin, and spermine. In one embodiment, the PLC inhibitor is U-73122 (1-[6-(17b-3-Methoxyestra-1,3,5(10)-trien-17-yl)amino)hexyl]-1H-pyrrole-2,5-dione). U-73122 has been shown to inhibit agonist-induced PLC activation in human platelets (Smith, et al., *J. Pharmacol. Exp. Ther.*, 253:688 (1990)) and neutrophils (Bleasdale, et al., *J. Pharmacol. Exp. Ther.*, 255:726 (1990)) with an $IC_{50}$ of about 1.0-2.1 µM.

The molecular structure for U-73122 is shown below:

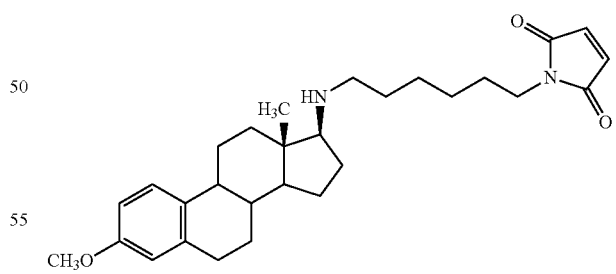

In other embodiments, the GSK3β phosphorylation antagonists are small molecules or peptides that inhibit or reduce the function of $IP_3$ that is produced by the enzymatic activity of PLC. Suitable antagonists include $IP_3$ receptor ($IP_3R$) inhibitors, including, but not limited to, 2-APB (2-Aminoethoxydiphenyl borate), xestospongin C, and TMB-8 (8-(N,N-Diethylamino)-octyl-3,4,5-trimethoxybenzoate). The molecular structure for 2-APB is shown below:

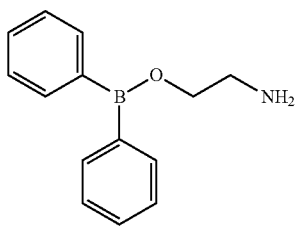 [SMILES: NCCOB(c1ccccc1)c1ccccc1]

The molecular structure for xestospongin C is shown below:

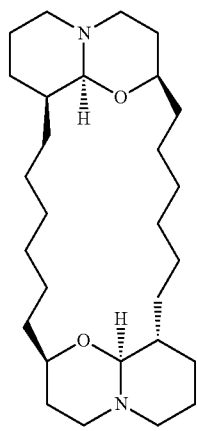 [SMILES: C1CCC[C@H]2CCCN3CC[C@@H](CCCCCC[C@@H]4CCCN5CC[C@@H](CC1)O[C@@H]45)O[C@@H]23]

The molecular structure for TMB-8 is shown below:

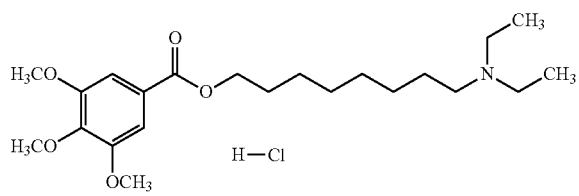 [SMILES: CCN(CC)CCCCCCCCOC(=O)c1cc(OC)c(OC)c(OC)c1 ; Cl]

c. Protein Tyrosine Kinases (PTKs)

In other embodiments, the GSK3β phosphorylation antagonists are small molecules or peptides that inhibit or reduce the enzymatic activity of PTKs. In some embodiments, the PTK inhibitors are broad-range PTK inhibitors. Many suitable PTK inhibitors are known in the art and are publicly available through a number of commercial sources.

Suitable PTK inhibitors include, but are not limited to, tyrphostin A23 ((3,4-dihydroxybenzylidene)malononitrile) and tyrphostin A47 (α-Cyano-(3,4-dihydroxy)thiocinnamide). In one embodiment, the PTK inhibitor is genistein (4',5,7-Trihydroxyisoflavone). Genistein is a broad-range PTK inhibitor that is competitive with respect to ATP and non-competitive with respect to the phosphate acceptor.

The molecular structure for genistein is shown below:

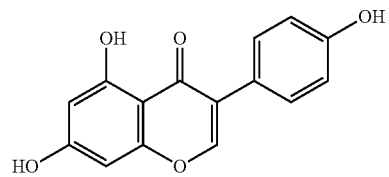 [SMILES: O=c1c(-c2ccc(O)cc2)coc2cc(O)cc(O)c12]

d. Gαq

In other embodiments, the GSK3β phosphorylation antagonists are small molecules or peptides that inhibit or reduce the activity of Gαq. Suitable Gαq include, but are not limited to, GP-2A (Arg-Pro-Lys-Pro-Gln-Gln-D-Trp-Phe-D-Trp-D-Trp-Met-NH$_2$), and YM-254890. YM-254890 is a cyclic depsipeptide containing uncommon amino acids; β-hydroxyleucine (two residues), N,O-dimethylthreonine and N-methyldehydroalanine.

The structure of YM-254890 is shown below:

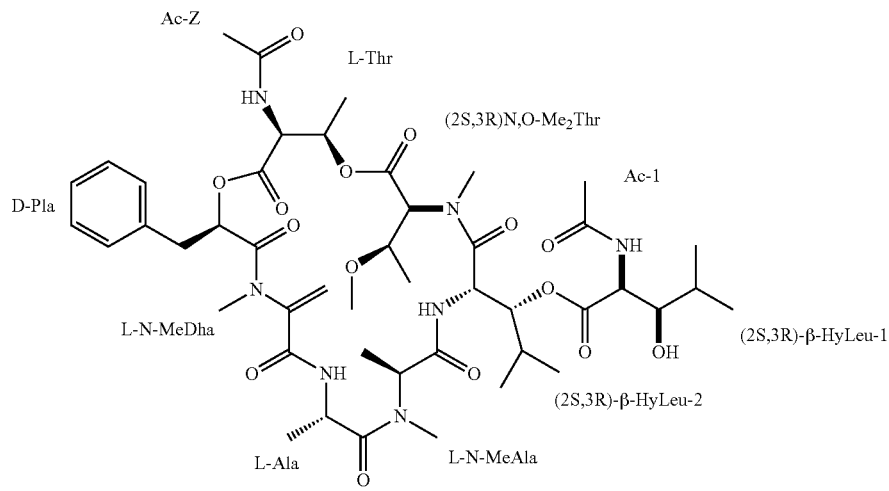

e. Glucocorticoid Receptor (GR)

In other embodiments, the GSK3β phosphorylation antagonists are small molecules or peptides that inhibit or reduce the activity of the glucocorticoid receptor. Many suitable GR inhibitors are known in the art and are publicly available through a number of commercial sources.

Suitable GR inhibitors include, but are not limited to, RU-486 (mifepistone) ((11b,17b)-11-(4-(Dimethylamino) phenyl)-17-hydroxy-17-(1-propynyl)estra-4,9-dien-3-one), RU-40555, RU-38486, ORG 34116, ORG 34850 and ORG 34517. In a preferred embodiment, the GR inhibitor is RU-486. The examples demonstrate that RU-486 effectively blocks induction of LEF/TCF-mediated transcription and expression of c-myc in response to GC administration.

The structure of RU-486 is shown below:

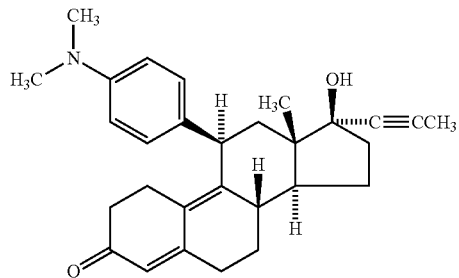

f. Other Small Molecule Antagonists

It will be appreciated that additional bioactive agents may be screened for antagonistic activity. In some embodiments, candidate bioactive agents are screened for their ability to inhibit or reduce phosphorylation of GSK3β in cells, such as keratinocytes, contacted with a glucocorticoid, such as dexamethasone. Candidate bioactive agents may additionally be screened for their ability to inhibit or reduce nuclearization of β-catenin and/or induction of c-myc in cells, such as keratinocytes, contacted with a glucocorticoid, such as dexamethasone.

The term "candidate agent" or "candidate bioactive agent" as used herein describes any molecule, e.g., protein, small organic molecule, small inorganic molecule, organo-metallic molecules, carbohydrates (including polysaccharides), polynucleotide, lipids, etc. Generally, a plurality of assay mixtures is run in parallel with different agent concentrations to obtain a differential response to the various concentrations. Typically, one of these concentrations serves as a negative control, i.e., at zero concentration or below the level of detection. In addition, positive controls, i.e. the use of agents known to inhibit phosphorylation of GSK3β may be used.

Candidate agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced.

Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

When a crude extract is found to have a desired activity, further fractionation of the positive lead extract may be necessary to isolate chemical constituents responsible for the observed effect. Thus, the goal of the extraction, fractionation, and purification process is the careful characterization and identification of a chemical entity within the crude extract having the desired activity. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases or conditions, such as those disclosed herein.

Candidate agents encompass numerous chemical classes, but are most often organic molecules, e.g., small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, for example, at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. In a further embodiment, candidate agents are peptides.

In some embodiments, the candidate agents are proteins. In some aspects, the candidate agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening using the methods herein. The libraries can be bacterial, fungal, viral, and vertebrate proteins, and human proteins.

2. Inhibitory Nucleic Acids

In other embodiments, the GSK3β phosphorylation antagonists are inhibitory nucleic acids that downregulate the expression of signaling molecules that contribute to the phosphorylation of GSK3β in response to GCs in keratinocytes. In some embodiments, the inhibitory nucleic acids downregulate the expression of signaling molecules upstream of GSK3β phosphorylation, as shown in FIG. 1. Suitable inhibitory nucleic acids include, but are not limited to, inhibitory nucleic acids that downregulate the expression of glucocorticoid receptors (GRs), Gαq, phospholipase C (PLC), or protein kinase C (PKC).

The terms "inhibitory ribonucleic acid" or "inhibitory RNA" refer to RNAs specific for target RNAs that reduce or inhibit the expression of the target RNA. Representative inhibitory nucleic acids include, but are not limited to dsRNA, siRNA, shRNA, miRNA, piRNA, external guide sequences, ribozymes, and other short catalytic RNAs. Expression of the target nucleic acid can be inhibited at the transcriptional or translational level.

Inhibitory RNAs are configured to hybridize to target mRNAs and modulate their expression or integrity. Inhibitory RNAs can modulate target mRNA expression through several means, including directly catalyzing target mRNA degradation, causing the recruitment of cellular proteins and enzymes that mediate mRNA degradation, inhibiting or reducing the translation of target mRNA, or otherwise reducing the stability of target mRNA. Inhibitory RNAs can be single-stranded or double-stranded. Exemplary inhibitory RNAs include, but are not limited to, dsRNA, siRNA, shRNA, mlRNA, piRNA, external guide sequences, ribozymes, and other short catalytic RNAs.

Inhibitory RNAs are complementary to their target RNAs. The term "complementary", as used herein, refers to the capacity of two nucleotides to pair precisely with each other. This term may also be used to refer to oligonucleotides which exhibit the ability of pairing precisely with each other. For example, if the nucleotides located at a certain position on two oligonucleotides are capable of hydrogen bonding, then the oligonucleotides are considered to be complementary to each other at that position. The inhibitory RNAs and the target RNAs are complementary to each other when a sufficient number of corresponding positions in each molecule are occupied by nucleotides which can hydrogen bond with each other. Thus, "complementary" is a term that is used to indicate a sufficient degree of complementarity or precise paring such that stable and specific binding may occur between the inhibitory RNA and the target RNA. It is understood in the art that the sequence of an inhibitory oligonucleotide compound need not be 100 percent complementary to that of its target RNA. A sufficient degree of complementarity prevents non-specific binding of the inhibitory oligonucleotide compound to non-target sequences under conditions in which specific binding is desired, i.e. under physiological conditions.

Inhibitory RNAs can contain any known base analogs including, but not limited to, 4-acetylcytosine, 8-hydroxy-N-6-methyladenosine, aziridinylcytosine, pseudoisocytosine, 5-(carboxyhydroxylmethyl) uracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to O-methyl, amino-, and fluoro-modified analogs.

Inhibitory RNAs can be produced using methods known to those skilled in the art. They can be chemically synthesized, produced by in vitro transcription; expressed in cells from an expression plasmid or viral vector; or expressed in cells from a PCR-derived expression cassette. In vitro synthesis may be chemical or enzymatic, for example, using cloned RNA polymerase (e.g., T3, T7, SP6) for transcription of the endogenous DNA (or cDNA) template, or a mixture of both. SiRNAs can also be produced by digestion of long dsRNA by an RNase III family enzyme (e.g., Dicer, RNase III). In a preferred embodiment, the inhibitory RNAs are obtained synthetically, for example, by chemically synthesizing a nucleic acid by any method of synthesis known to the skilled artisan. The synthesized inhibitory RNAs can then be purified by any method known in the art. Methods for chemical synthesis of nucleic acids include in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In vivo, inhibitory RNAs may be synthesized using recombinant techniques well known in the art (see e.g., Sambrook, et al., Molecular Cloning; A Laboratory Manual, Third Edition (2001). For example, bacterial cells can be transformed with an expression vector which comprises the DNA template from which the inhibitory RNAs are to be derived. The RNA can be purified by extraction with a solvent (such as phenol/chloroform) or resin, precipitation (for example in ethanol), electrophoresis, chromatography, or a combination thereof.

Methods for producing inhibitory RNAs that target mRNAs of known sequence are known in the art. One of skill in the art could readily produce inhibitory RNAs that downregulate the expression of any chosen mRNA in host using information that is publicly available, including the known nucleic acid sequence of the target mRNA. Nucleotide sequences for mRNAs that encode for GR, Gαq, PLC and PKC are well known in the art.

i. siRNA and sRNA

In one embodiment, the inhibitory RNAs are siRNAs or shRNAs. The term "siRNA" means a small interfering RNA that is a short-length double-stranded RNA that is not toxic. Generally, there is no particular limitation in the length of siRNA as long as it does not show toxicity. "siRNAs" can be, for example, 15 to 49 bp, preferably 15 to 35 bp, and more preferably 21 to 30 by long.

Inhibitory nucleic acids and methods of producing them are well known in the art. siRNA design software is available for example at http://i.cs.hku.hk/~sirna/software/sirna.php. The sequence of at least one strand of the siRNA contains a region complementary to at least a part of the target mRNA sufficient for the siRNA to specifically hybridize to the target mRNA. In one embodiment, the siRNA is substantially identical to at least a portion of the target mRNA. "Identity", as known in the art, is the relationship between two or more polynucleotide (or polypeptide) sequences, as determined by comparing the sequences. In the art, identity also means the degree of sequence relatedness between polynucleotide sequences, as determined by the match between strings of such sequences. Identity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, N.J., 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two polynucleotide sequences, the term is well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., *SIAM J. Applied Math.*, 48: 1073 (1988). Methods commonly employed to determine identity between sequences include, but are not limited to, those disclosed in Carillo, H., and Lipman, D., *SIAM J. Applied Math.*, 48:1073 (1988). Preferred methods to determine identity are designed to give the largest match between the sequences tested. Methods to determine identity are codified in computer programs. Computer program methods to determine identity between two sequences include, but are not limited to, GCG program package (Devereux, J., et al., *Nucleic Acids Research*, 12(1): 387 (1984)), BLASTP, BLASTN, and FASTA (Atschul, S. F. et al., *J. Molec. Biol.*, 215: 403 (1990)). Another software package well known in the art for carrying out this procedure is the CLUSTAL program. It compares the sequences of two polynucleotides and finds the optimal alignment by inserting spaces in either sequence as appropriate. The identity for an optimal alignment can also be calculated using a software package such as BLASTx. This program aligns the largest stretch of similar sequence and assigns a value to the fit. For any one pattern comparison several regions of similarity may be found, each having a different score. One skilled in the art will appreciate that two polynucleotides of different lengths may be compared over the entire length of the longer fragment. Alternatively small regions may be compared. Normally sequences of the same length are compared for a useful comparison to be made.

In one embodiment, the inhibitory nucleic acid has 100% sequence identity with at least a part of the target mRNA. However, inhibitory nucleic acids having 70%, 80% or greater than 90% or 95% sequence identity may be used. Thus sequence variations that might be expected due to genetic mutation, strain polymorphism, or evolutionary divergence can be tolerated.

The duplex region of the RNA may have a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

The double-stranded RNA portions of siRNAs in which two RNA strands pair up are not limited to the completely paired ones, and may contain nonpairing portions due to mismatch (the corresponding nucleotides are not complementary) or bulge (lacking in the corresponding complementary nucleotide on one strand). Nonpairing portions can be contained to the extent that they do not interfere with siRNA formation. Suitable siRNAs can contain one or more modified bases, or have a modified a backbone to increase stability or for other reasons. For example, the phosphodiester linkages of natural RNA may be modified to include at least one of a nitrogen or sulfur heteroatom. siRNAs comprising unusual bases, including, but not limited to inosine, or modified bases, such as tritylated bases, can be used. The term "siRNA", as used herein, embraces such chemically, enzymatically or metabolically modified forms of siRNA.

The terminal structure of siRNA may be either blunt or cohesive (overhanging) as long as siRNA can silence, reduce, or inhibit the target gene expression due to its RNAi effect. The cohesive (overhanging) end structure is not limited only to the 3' overhang, and the 5' overhanging structure may be included as long as it is capable of inducing the RNAi effect. The number of overhanging nucleotide can be any numbers as long as the overhang is capable of inducing the RNAi effect. For example, the overhang can consist of 1 to 8, or preferably 2 to 4 nucleotides.

The terminal structure of the siRNA is not necessarily the cut off structure at both ends as described above, and may have a stem-loop structure in which ends of one side of double-stranded RNA are connected by a linker RNA. siRNAs containing a linker RNA that forms a hairpin structure are referred to as short hairpin RNAs, or shRNAs. The length of the double-stranded RNA region (stem-loop portion) can be, for example, 15 to 49 bp, preferably 15 to 35 bp, and more preferably 21 to 30 by long. Alternatively, the length of the double-stranded RNA region that is a final transcription product of siRNAs to be expressed is, for example, 15 to 49 bp, preferably 15 to 35 bp, and more preferably 21 to 30 by long. Furthermore, there is no particular limitation in the length of the linker as long as it has a length so as not to hinder the pairing of the stem portion. For example, for stable pairing of the stem portion and suppression of the recombination between DNAs coding for the portion, the linker portion may have a clover-leaf tRNA structure. Even though the linker has a length that hinders pairing of the stern portion, it is possible, for example, to construct the linker portion to include introns so that the introns are excised during processing of precursor RNA into mature RNA, thereby allowing pairing of the stem portion.

ii. miRNA

Micro RNAs (referred to as "miRNAs") are small non-coding RNAs, belonging to a class of regulatory molecules found in plants and animals that control gene expression by binding to complementary sites on target messenger RNA (mRNA) transcripts. miRNAs are generated from large RNA precursors (termed pri-miRNAs) that are processed in the nucleus into approximately 70 nucleotide pre-miRNAs, which fold into imperfect stem-loop structures (Lee, Y., et al., Nature (2003) 425(6956):415-9). The pre-miRNAs undergo an additional processing step within the cytoplasm where mature miRNAs of 18-25 nucleotides in length are excised from one side of the pre-miRNA hairpin by ah RNase III enzyme, Dicer (Hutvagner, G., et al., Science (2001) 12:12 and Grishok, A., et al., Cell (2001) 106(1):23-34). MiRNAs have been shown to regulate gene expression in two ways. First, miRNAs that bind to protein-coding mRNA sequences that are exactly complementary to the miRNA induce the RNA-mediated interference (RNAi) pathway. Messenger RNA targets are cleaved by ribonucleases in the ribonucleoprotein complex known as the RISC complex. This mechanism of miRNA-mediated gene silencing has been observed in plants (Hamilton, A. J. and D. C. Baulcombe, Science (1999) 286(5441):950-2 and Reinhart, B. J., et al., *MicroRNAs in plants*. Genes and Dev. (2002) 16:1616-1626), and in animals (Yekta, S., I. H. Shih, and D. P. Bartel, Science (2004) 304(5670):594-6). In the second mechanism, miRNAs that bind to imperfect complementary sites on messenger RNA transcripts direct gene regulation at the posttranscriptional level but do not cleave their mRNA targets. MiRNAs identified in both plants and animals use this mechanism to exert translational control of their gene targets (Bartel, D. P., Cell (2004) 116(2):281-97).

Preferred miRNAs have at least 80%, typically at least 90%, even more typically at least 95% sequence identity with the target mRNA. Naturally occurring microRNAs that regulate target RNAs, pri-miRNA, pre-miRNA, mature miRNA or fragments of variants thereof that retain the biological activity of the mature miRNA and DNA encoding a pri-miRNA, pre-miRNA, mature miRNA, fragments or variants thereof, or regulatory elements of the miRNA, have been identified. The size of the miRNA is typically from 21 nucleotides to 170 nucleotides, although nucleotides of up to 2000 nucleotides can be utilized. In a preferred embodiment the size range of the pre-miRNA is between 70 to 170 nucleotides in length and the mature miRNA is between 21 and 25 nucleotides in length.

iii. piRNA

Recent studies have revealed a new class of 24- to 30-nt RNAs that are generated by a Dicer-independent mechanism and that interact with a subset of Argonaute proteins related to Piwi. Studies in *Drosophila* have identified five Argonaute proteins: Ago1, Ago2, Ago3, Piwi, and Aubergine (Aub). Ago1 and Ago2 are ubiquitously expressed, whereas the expression of Piwi, Aub, and Ago3 are germ line-specific. Ago1 associates with miRNAs to regulate endogenous gene expression, and Ago2 serves as the slicer for siRNA-mediated gene silencing. Piwi, Aub, and Ago3 have been recently reported to interact with 24- to 30-nt small RNAs known as rasiRNAs. Murine Ago1, Ago2, Ago3, and Ago4 are associated with miRNAs, while the Piwi orthologs, MIWI, MILL and MIWI2, are found in germ line cells.

Like other members of the Ago family, Piwi proteins associate with small RNAs that act as guides in silencing target mRNA. These Piwi-interacting RNAs are called Piwi-interacting RNA (piRNA). These small RNAs associated with Piwi ribonucleoproteins (RNPs) have been cloned and sequence analysis of piRNAs shows a high percentage of uridine residues at the 5' termini (Gunawardane, et al., *Science*, 315(5818):1587-90 (2007), and genomic mapping shows that piRNAs are concentrated at a few loci (Brennecke et al., *Cell*, 128(6):1089-103 (2007)).

Primary transcripts for piRNAs are generated from the transposon regulatory regions of heterochromatin. These piRNAs are anti-sense, or complementary to transposon transcripts, and associated with both Piwi and Aub to trigger the amplification loop. Piwi/Aub cleaves target transposon transcripts between 10 and 11 nt from the 5' end of anti-sense piRNA and subsequently generates Ago3-associated sense piRNA. Ago3 functions as another slicer, which recognizes the complementary sequence of piRNA cluster transcripts, and generates more Piwi/Aub-associated anti-sense strand piRNA. piRNAs are thought to function with Piwis endogenously to maintain transposon silencing.

iv. External Guide Sequences (EGSs)

Ribonuclease P (RNase P) is a ribonucleoprotein complex found in all organisms. It is highly active in cells and is responsible for the maturation of 5' termini of all tRNAs, which account for approximately 2% of total cellular RNA. Human RNase P has at least nine polypeptides and a RNA subunit (H1RNA). One of the unique features of RNase P is its ability to recognize structures, rather than the sequences, of substrates. This allows RNase P to hydrolyze different natural substrates in vivo or in vitro. Accordingly, any complex of two RNA molecules that resembles a tRNA molecule can be recognized and cleaved by RNase P. One of the RNA molecules is called the external guide sequence (EGS). An mRNA sequence can be targeted for RNase P cleavage by using EGSs to hybridize with the target RNA and direct RNase P to the site of cleavage. The EGSs used to direct human RNase P for targeted cleavage resemble three-quarters of a tRNA molecule and consist of two sequence elements: a targeting sequence complementary to the mRNA sequence and a guide sequence, which is a portion of the natural tRNA sequence and is required for RNase P recognition.

An EGS is designed to base pair through hydrogen bonding mechanism with a target mRNA to form a molecular structure similar to that of a transfer RNA (tRNA). The EGS/mRNA target is then cleaved and inactivated by RNAse P. EGS are not consumed in this reaction, but instead can recycle as a catalyst through multiple cycles of target mRNA cleavage leading to target inactivation more effectively than conventional anti-sense DNA oligonucleotides. EGS combine the specificity of conventional antisense DNA for gene targeting with the catalytic potency of RNAse P. RNAse P is present in abundant quantities in all viable eukaryotic cells where it serves to process transfer RNA (tRNA) by cleavage of a precursor transcript.

Small RNA sequences have been described that target eukaryotic mRNA for degradation by endogenous RNAse P, a ubiquitous cellular enzyme that generates mature transfer RNA (tRNA) from precursor transcripts (Gopalan, et al., *J. Biol. Chem.* 277:6759-6762 (2002); Guerrier-Takada and Altman, *Methods Enzymol.* 313:442-456 (2000); and Plehn-Dujowich and Altman, *PNAS USA* 95:7327-7332 (1998)). A small RNA termed an External Guide Sequence (EGS) can be designed that mimics certain structural features of a tRNA molecule when it forms a bimolecular complex with another RNA sequence contained within a cellular messenger RNA (mRNA). Thus, any mRNA can in principle be recognized as a substrate for RNAse P with both the EGS and RNAse P participating as cocatalysts although due to the complexity of the binding and cleavage steps the kinetics of the reaction are difficult to predict in vitro or in vivo (Gopalan, et al., *J. Biol. Chem.* 277:6759-6762 (2002) and Guerrier-Takada and Altman, *Methods Enzymol*, 313:442-456 (2000)).

Design of an EGS requires both knowledge of the mRNA primary sequence to be cleaved by RNAse P as well as the secondary structure of the mRNA sequences in the mRNA. EGS sequences must be complementary to the primary sequence of the targeted mRNA and the sequences in the mRNA must be exposed in a single-stranded conformation within the mRNA secondary structure in order to bind to the EGS. Secondary structure of target mRNA can be approximated by computer modeling or determined empirically using nucleases or other RNA cleaving reagents well known to one of ordinary skill in the art. This analysis may be useful in locating regions of mRNA for targeting with complementary oligonucleotides including conventional DNA antisense oligonucleotides and catalytic RNA.

RNAase P is a ribonucleoprotein having two components, an RNA component and a protein component. The RNA component of RNAase P is responsible for the catalytic cleavage which forms the mature 5' ends of all transfer RNAs. RNAase P is endogenous to all living cells that have been examined. During the studies on recognition of substrate by RNAase P, it was found that *E. coli* RNAase P can cleave synthetic tRNA-related substrates that lack certain domains, specifically, the D, TψC and anticodon stems and loops, of the normal tRNA structure. For bacterial RNAse P a half-turn of an RNA helix and a 3' proximal CCA sequence contain sufficient recognition elements to allow the reaction to proceed. Using these principles, any RNA sequence can be converted into a substrate for bacterial RNAase P by using an external guide sequence, having at its 5' terminus nucleotides complementary to the nucleotides 3' to the cleavage site in the RNA to be cleaved and at its 5' terminus the nucleotides NCCA (N is any nucleotide).

EGS for promoting RNAase P-mediated cleavage of RNA has also been developed for use in eukaryotic systems as described by U.S. Pat. No. 5,624,824 to Yuan, et al., U.S. Pat. No.6,610,478 to Table, et al., WO 93/22434 to Yale University, WO 95/24489 to Yale University, and WO 96/21731 to Innovir Laboratories, Inc. As used herein, "external guide sequence" and "EGS" refer to any oligonucleotide or oligonucleotide analog that forms, in combination with a target RNA, a substrate for RNAase P.

An external guide sequence for promoting cleavage by RNAase P contains sequences which are complementary to the target RNA and which forms secondary and tertiary structures similar to portions of a tRNA molecule. In eukaryotes, including mammals, tRNAs are encoded by families of genes that are 73 to 150 base pairs long. tRNAs assume a secondary structure with four base paired stems known as the cloverleaf structure. The tRNA contains a stem, a D loop, a Variable loop, a TψC loop, and an anticodon loop. In one form, the EGS contains at least seven nucleotides which base pair with the target sequence 3' to the intended cleavage site to form a structure like the stem, nucleotides which base pair to form stem and loop structures similar to the TψC loop, the Variable loop and the anticodon loop, followed by at least three nucleotides that base pair with the target sequence to form a structure like the D loop.

Preferred guide sequences for eukaryotic RNAase P consist of a sequence which, when in a complex with the target RNA molecule, forms a secondary structure resembling that of a tRNA cloverleaf or parts thereof. The desired secondary structure is determined using conventional Watson-Crick base pairing schemes to form a structure resembling a tRNA. Since RNAse P recognizes structures as opposed to sequences, the specific sequence of the hydrogen bonded regions is less critical than the desired structure to be formed. The EGS and the target RNA substrate should resemble a sufficient portion of the tRNA secondary and tertiary structure to result in cleavage of the target RNA by RNAase P. The sequence of the EGS can be derived from any tRNA. The sequences and structures of a large number of tRNAs are well known to one of ordinary skill in the art and can be found at least at http://rna.wustl.edu/tRNAdb/. The sequence obtained from the stern of the tRNA is altered to be complementary to the identified target RNA sequence. Target RNA is mapped by techniques well known to one of ordinary skill in the art for the consensus sequence. Such techniques include digestion of the target mRNA with T1 nuclease. Digestion with T1 nuclease cleaves RNA after guanine (G) residues that are exposed in solution and single-stranded, but not after G residues that are buried in the RNA secondary structure or base paired into double-stranded regions. The reaction products form a ladder after size fractionantion by gel-electrophoresis. A T1 sensitive site is detected as a dark band is compared to the target mRNA sequence to identify RNAse P consensus sequences. The complimentary sequence from the target mRNA is used for the EGS. The complementary sequences may consist of as few as seven nucleotides, but preferably include eleven nucleotides, in two sections which base pair with the target sequence and which are preferably separated by two unpaired nucleotides in the target sequence, preferably UU, wherein the two sections are complementary to a sequence 3' to the site targeted for cleavage.

The remaining portion of the guide sequence, which is required to cause RNAase P catalytic RNA to interact with the EGS/target RNA complex, is herein referred to as an RNAase P binding sequence. The anticodon loop and the Variable loop can be deleted and the sequence of the TψC loop can be changed without decreasing the usefulness of the guide sequence. External guide sequences can also be derived using in vitro evolution techniques (see U.S. Pat. No. 5,624,824 to Yuan, et al. and WO 95/24489 to Yale University).

v. Ribozymes and Other Catalytic RNAs

In another embodiment, the inhibitory RNA is a catalytic RNA, or a ribozyme. Ribozymes are described, for example, in PCT International Publication WO 90/11364, published Oct. 4, 1990; Sarver et al, Science, 247:1222-1225 (1990). While ribozymes that cleave mRNA at site specific recognition sequences can be used to degrade target mRNAs the use of hammerhead ribozymes is preferred. Hammerhead ribozymes cleave mRNAs at locations dictated by flanking regions that form complementary base pairs with the target mRNA. The sole requirement is that the target mRNA has the following sequence of two bases: 5'-UG-3'. The construction and production of hammerhead ribozymes is well known in the art and is described more fully in Haseloff and Gerlach, Nature, 334:585-591 (1988). There are usually numerous potential hammerhead ribozyme cleavage sites within each nucleotide sequence of a target mRNA of known sequence. Preferably, the ribozyme is engineered so that the cleavage recognition site is located near the 5' end of the target mRNA. This functions to increase efficiency and minimize the intracellular accumulation of non-functional mRNA transcripts.

B. Carriers

1. Topical Carriers

The GSK3β phosphorylation antagonists can be administered using a syringe, bandage, transdermal patch, insert, or syringe-like applicator, as a liquid, spray, aerosol, ointment, foam, cream, gel, paste, or powder/talc or other solid.

The GSK3β phosphorylation antagonists may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents include water and physiologically acceptable buffered saline solutions such as phosphate buffered saline solutions with a substantially neutral pH. Additives may be mixed in with the formulation for maximum or desired efficacy of the delivery system or for the comfort of the patient. Such additives include, for example, lubricants, plasticizing agents, preservatives, gel formers, film formers, cream formers, disintegrating agents, coatings, binders, vehicles, coloring agents, odor controlling agents, humectants, viscosity controlling agents, pH-adjusting agents, and similar agents.

In a preferred embodiment, the compositions contain sufficient amounts of at least one pH buffering agent to ensure that the composition has a final pH of about 3 to about 11, preferably between 6 and 8, most preferably at or near the pH of the skin. Suitable pH modifying agents include, but are not limited to, sodium hydroxide, citric acid, hydrochloric acid, acetic acid, phosphoric acid, succinic acid, sodium hydroxide, potassium hydroxide, ammonium hydroxide, magnesium oxide, calcium carbonate, magnesium carbonate, magnesium aluminum silicates, hydroxyapatite, malic acid, potassium citrate, sodium citrate, sodium phosphate, lactic acid, gluconic acid, tartaric acid, 1,2,3,4-butane tetracarboxylic acid, fumaric acid, diethanolamine, monoethanolamine, sodium carbonate, sodium bicarbonate, triethanolamine, and combinations thereof.

Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

The percent by weight of the active agents present in a formulation will depend on various factors, but generally will be from about 0.01% to about 98% of the total weight of the formulation, and typically about 0.1 to about 90% by weight, more typically less than 50%, most typically in the range of 0.5 to 10%. Reference is also made to the following examples which demonstrate the dose response curves for the formulations applied to appropriate animal models.

i. Emulsions, Ointments and Creams

The compositions can be formulated as emulsions for topical application. An emulsion contains one liquid distributed the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

Suitable surfactants include, but are not limited to, anionic surfactants, non-ionic surfactants, cationic surfactants, and amphoteric surfactants. Examples of anionic surfactants include, but are not limited to, ammonium lauryl sulfate, sodium lauryl sulfate, ammonium laureth sulfate, sodium laureth sulfate, alkyl glyceryl ether sulfonate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium and ammonium salts of coconut alkyl triethylene glycol ether sulfate; tallow alkyl triethylene glycol ether sulfate, tallow alkyl hexaoxyethylene sulfate, disodium N-octadecylsulfosuccinnate, disodium lauryl sulfosuccinate, diammonium lauryl sulfosuccinate, tetrasodium N-(1,2-dicarboxyethyl)-N-octadecylsulf-osuccinnate, diamyl ester of sodium sulfosuccinic acid, dihexyl ester of sodium sulfosuccinic acid, dioctyl esters of sodium sulfosuccinic acid, docusate sodium, and combinations thereof.

Examples of nonionic surfactants include, but are not limited to, polyoxyethylene fatty acid esters, sorbitan esters, cetyl octanoate, cocamide DEA, cocamide MEA, cocamido propyl dimethyl amine oxide, coconut fatty acid diethanol amide, coconut fatty acid monoethanol amide, diglyceryl diisostearate, diglyceryl monoisostearate, diglyceryl monolaurate, diglyceryl monooleate, ethylene glycol distearate, ethylene glycol monostearate, ethoxylated castor oil, glyceryl monoisostearate, glyceryl monolaurate, glyceryl monomyristate, glyceryl monooleate, glyceryl monostearate, glyceryl tricaprylate/caprate, glyceryl triisostearate, glyceryl trioleate, glycol distearate, glycol monostearate, isooctyl stearate, lauramide DEA, lauric acid diethanol amide, lauric acid monoethanol amide, lauric/myristic acid diethanol amide, lauryl dimethyl amine oxide, lauryl/myristyl amide DEA, lauryl/myristyl dimethyl amine oxide, methyl gluceth, methyl glucose sesquistearate, oleamide DEA, PEG-distearate, polyoxyethylene butyl ether, polyoxyethylene cetyl ether, polyoxyethylene lauryl amine, polyoxyethylene lauryl ester, polyoxyethylene lauryl ether, polyoxyethylene nonylphenyl ether, polyoxyethylene octyl ether, polyoxyethylene octylphenyl ether, polyoxyethylene oleyl amine, polyoxyethyelen oleyl cetyl ether, polyoxyethylene oleyl ester, polyoxyethylene oleyl ether, polyoxyethylene stearyl amine, polyoxyethylene stearyl ester, polyoxyethylene stearyl ether, polyoxyethylene tallow amine, polyoxyethylene tridecyl ether, propylene glycol monostearate, sorbitan monolaurate, sorbitan monooleate, sorbitan monopalmitate, sorbitan monostearate, sorbitan sesquioleate, sorbitan trioleate, stearamide DEA, stearic acid diethanol amide, stearic acid monoethanol amide, laureth-4, and combinations thereof.

Examples of amphoteric surfactants include, but are not limited to, sodium N-dodecyl-γ-alanine, sodium N-lauryl-γ-iminodipropionate, myristoamphoacetate, lauryl betaine, lauryl sulfobetaine, sodium 3-dodecyl-aminopropionate, sodium 3-dodecylaminopropane sulfonate, sodium lauroamphoacetate, cocodimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyeth-yl betaine, oleamidopropyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and combinations thereof.

Examples of cationic surfactants include, but are not limited to, behenyl trimethyl ammonium chloride, bis(acyloxyethyl) hydroxyethyl methyl ammonium methosulfate, cetrimonium bromide, cetrimonium chloride, cetyl trimethyl ammonium chloride, cocamido propylamine oxide, distearyl dimethyl ammonium chloride, ditallowdimonium chloride, guar hydroxypropyltrimonium chloride, lauralkonium chloride, lauryl dimethylamine oxide, lauryl dimethylbenzyl ammonium chloride, lauryl polyoxyethylene dimethylamine oxide, lauryl trimethyl ammonium chloride, lautrimonium chloride, methyl-1-oleyl amide ethyl-2-oleyl imidazolinium methyl sulfate, picolin benzyl ammonium chloride, polyquaternium, stearalkonium chloride, sterayl dimethylbenzyl ammonium chloride, stearyl trimethyl ammonium chloride, trimethylglycine, and combinations thereof.

Suitable suspending agents include, but are not limited to, alginic acid, bentonite, carbomer, carboxymethylcellulose and salts thereof, hydroxyethylcellulose, hydroxypropylcellulose, microcrystalline cellulose, colloidal silicon dioxide, dextrin, gelatin, guar gum, xanthan gum, kaolin, magnesium aluminum silicate, maltitol, triglycerides, methylcellulose, polyoxyethylene fatty acid esters, polyvinylpyrrolidone, propylene glycol alginate, sodium alginate, sorbitan fatty acid esters, tragacanth, and combinations thereof.

Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable antioxidants include, but are not limited to, butylated hydroxytoluene, alpha tocopherol, ascorbic acid, fumaric acid, malic acid, butylated hydroxyanisole, propyl gallate, sodium ascorbate, sodium metabisulfite, ascorbyl palmitate, ascorbyl acetate, ascorbyl phosphate, Vitamin A, folic acid, flavons or flavonoids, histidine, glycine, tyrosine, tryptophan, carotenoids, carotenes, alpha-Carotene, beta-Carotene, uric acid, pharmaceutically acceptable salts thereof, derivatives thereof, and combinations thereof.

Suitable chelating agents include, but are not limited to, EDTA, disodium edetate, trans-1,2-diaminocyclohexane-N,N,N',N'-tetraaceticacid monohydrate, N,N-bis(2-hydroxyethyl)glycine, 1,3-diamino-2-hydroxypropanet-N,N,N',N'-te-traacetic acid, 1,3-diaminopropane-N,N,N',N'-tetraacetic acid, ethylenediamine-N,N'-diacetic acid, ethylenediamine-N,N'-dipropionic acid, ethylenediamine-N,N'-bis(methylenephosphonie acid), N-(2-hydroxyethyl)ethylenediamine-N,N',N'-triacetic acid, ethylenediamine-N,N,N',N'-tetrakis(methylenephosponic acid), O,O'-bis(2-aminoethypethyleneglycol-N,N,N'N'-tetraacetic acid, N,N-bis(2-hydroxybenzyl)ethylenediamine-N,N-diacetic acid, 1,6-hexamethylenediamine-N,N,N',N'-tetraacetic acid, N-(2-hydroxyethyl)iminodiacetic acid, iminodiacetic acid, 1,2-diaminopropane-N,N,N',N'-tetraacetic acid, nitrilotriacetic acid, nitrilotripropionic acid, nitrilotris(methylenephosphotic acid), 7,19,30-frioxa-1,4,10,13,16,22,27,33-octaazabicyclo[11,11,11] pentatriacontane hexahydrobromide, triethylenetetramine-N,N,N',N'',N''',N''''-hexaacetic acid, and combinations thereof.

Suitable emollients include, but are not limited to, myristyl lactate, isopropyl palmitate, light liquid paraffin, cetearyl alcohol, lanolin, lanolin derivatives, mineral oil, petrolatum, cetyl esters wax, cholesterol, glycerol, glycerol monostearate, isopropyl myristate, lecithin, and combinations thereof thereof.

Suitable humectants include, but are not limited to, glycerin, butylene glycol, propylene glycol, sorbitol, triacetin, and combinations thereof.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays are conveniently delivered from pressurized packs, for example, via a specially shaped closure.

Oil-In-Water emulsions can also be utilized in the compositions, patches, bandages and articles. These systems are semisolid emulsions, micro- emulsions, or foam emulsion systems. Usually such a system has a "creamy white" appearance. Typically, the internal oil phase is in the range in percentage composition of about 10% to about 40% oil by weight and the external phase may contain 80% or more water. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes. These can be made with anionic, cationic, nonionic or amphoteric surfactants, or with combinations especially of the nonionic surfactants.

ii. Inserts

In some embodiments, the GSK3β phosphorylation antagonists can be formulated with oleaginous bases or ointments to form a semisolid composition with a desired shape. For example, the composition can be shaped for easy application to, or insertion into, a wound, ulcer, puncture wound or surgical site. This class of formulations comprises the active ingredients and hydrocarbon-based semisolids. In addition to the active ingredients, these semisolid compositions can contain dissolved and/or suspended bactericidal agents, preservatives and/or a buffer system. The petrolatum component in these bases can be any paraffin ranging in viscosity from mineral oil employing incorporated isobutylene, colloidal silica, or stearate salts to paraffin waxes. White and yellow petrolatums are examples of such systems. Bases of this class can be made by incorporating high-melting waxes into a fluid mineral oil via fusion or by incorporation of polyethylene into mineral oil at elevated temperature. Polysiloxanes (also known as silicones) are suitable for use in these bases and typically have a viscosity in the range of about 0.5 to 1o6centistokes. The organic entities attached to the polysiloxane are preferably lower molecular weight hydrocarbon moieties having from 1 to 8 carbons each, such as lower alkyl, lower alkenyl, phenyl and alkyl substituted phenyl, and phenyl(lower)alkyl, such as benzyl. In such a moiety, each lower alkyl or alkenyl group preferably has 1 to 3 carbons inclusive, such as in a dimethylsiloxane polymer.

Absorption bases can be used with such an oleaginous system. In addition to the active ingredients, additional ingredients with the capacity to emulsify a significant quantity of water are employed. Water-in-oil (w/o) emulsions can be formed wherein the external phase is oleaginous in character. Preservatives/bacteriostats, such as the parabens, buffer systems, etc. can be incorporated into these bases as emulsified aqueous solutions together with the active ingredient. Diverse additives are conveniently used as the emulsifier, and these include, but are not limited to, cholesterol, lanolin (which contains cholesterol and cholesterol esters and other emulsifiers), lanolin derivatives, beeswax, fatty alcohols, wool wax alcohols, low HLB (hydrophobellipophobe balance) emulsifiers, and assorted ionic and nonionic surfactants, singularly or in combination.

iii. Controlled Release Formulations

Controlled or sustained release can be achieved by the addition of time-release additives, such as polymeric structures, matrices, that are available in the art. A carrier used to deliver the disclosed GSK3β phosphorylation antagonists can include a mixture or coating of polymers that provide release of the active agents at a constant rate over a prolonged period of time.

In some embodiments, the carrier includes water-soluble pore forming agents, such as polyethylene glycol (PEG) that can be mixed with water insoluble polymers to increase the durability of the carrier, and to prolong the release of the active ingredients. Such a water-soluble pore-forming agent can be polyethylene glycol, polypropylene glycol, a mixture or polymer of sugars (lactose, sucrose, dextrose, etc.), salts, poloxamers, hydroxypropylcellulose, polyvinyl alcohol and other water-soluble food grade and other excipients.

The carrier may also include a water insoluble polymer. Examples of such polymers are ethylcellulose, acrylic resins, co-polymer of methacrylic acid and acrylic acid ethyl ester, polylactic acid, PLGA, polyurethane, polyethylene vinyl acetate copolymer, polystyrene- butadiene copolymer and silicone rubber, or mixtures thereof.

These rate controlling polymers can be applied using a continuous coating film during the process of spraying and drying with active agents. The rate controlling film prepared with such a polymer is stable during implantation. The film should have enough strength to withstand tear and inner osmotic pressure, and have the stability not to swell or hydrate during the implantation life. In one embodiment, the coating formulation is used to coat pellets comprising the active ingredients that are compressed to form a solid, biodegradable insert.

Alternatively, GSK3β phosphorylation antagonists can be delivered using a sustained release device. Either non-biodegradable or biodegradable matrices can be used for delivery of nucleic acids, although biodegradable matrices are preferred. These may be natural or synthetic polymers, although synthetic polymers are preferred due to the better characterization of degradation and release profiles. The polymer is selected based on the period over which release is desired, generally in the range of at least two to six weeks, although longer periods may be desirable. In some cases linear release may be most useful, although in others a pulse release or "bulk release" may provide more effective results. The polymer may be in the form of a hydrogel (typically absorbing up to about 90% by weight of water), and can optionally be crosslinked with multivalent ions or polymers.

GSK3β phosphorylation antagonists can be delivered partially by diffusion but mainly by degradation of the polymeric system. In this case, biodegradable polymers, bioerodible hydrogels, and protein delivery systems are particularly preferred. Examples of non-biodegradable polymers include ethylene vinyl acetate, poly(meth)acrylic acid, polyamides, copolymers and mixtures thereof. Examples of biodegradable polymers include synthetic polymers such as hydroxyacid polymers, for example, polymers of lactic acid and glycolic acid, polyanhydrides, poly(ortho)esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In one embodiment, the polymeric matrix is in the form of microparticles or nanoparticles. Microparticles can be in the form of microspheres, where the GSK3β phosphorylation antagonist is dispersed within a solid polymeric matrix, or microcapsules, where the core is of a different material than the polymeric shell, and the GSK3β phosphorylation antagonists is dispersed or suspended in the core, which may be liquid or solid in nature. Unless specifically defined herein, microparticles, microspheres, microcapsules, nanoparticles, nanospheres, and nanocapsules are used interchangeably.

Alternatively, the polymer may be cast as a thin slab or film, ranging from nanometers to four centimeters, a powder produced by grinding or other standard techniques, or even a gel such as a hydrogel. The matrices can be formed by solvent evaporation, spray drying, solvent extraction and other methods known to those skilled in the art.

In another embodiment, sustained release matrices are formed using fibrin. Fibrin-based biomaterial preparations can be used as provisional growth matrices for cells important in tissue repair during wound healing in vivo. The release of growth factor from fibrin-based biomaterials was demonstrated by Wong, et al., *Thromb Haemost.*, 89(3):573-82 (2003). Growth factor was incorporated into the fibrin biomaterials prior to formation of the clots. Clotting resulted in sustained release of growth factor causing angiogenic activity.

Another embodiment provides GSK3β phosphorylation antagonists incorporated in a conventional hydrophobic polymer matrix, e.g. of a polylactide, which is made more accessible for water by introducing a hydrophilic unit, e.g. of polyethyleneglycol, polyvinylalcohol, dextran or polymethacrylamide. The hydrophilic contribution to the amphipathic polymer is given by all the ethylene oxide groups in case of a polyethylene glycol unit, by the free hydroxyl groups in the case of a polyvinylalcohol unit or of a dextran unit, and by the amide groups in the case of a polymethyacrylamide unit.

2. Nucleic Acid Delivery Vehicles

GSK3β phosphorylation antagonists that are inhibitory nucleic acids can be introduced into the skin or other external tissues with agents that can facilitate uptake into epithelial cells using a variety of techniques that are available in the art. For example, nucleic acid GSK3β phosphorylation antagonists can be introduced into cells using mechanical methods, such as microinjection, liposome-mediated transfection, iontophoresis, or calcium phosphate precipitation. In one embodiment, the disclosed nucleic acid GSK3β phosphorylation antagonists are formulated in the form of a controlled release formulation or sustained release formulation administered topically or injected directly into the skin adjacent to or within the area to be treated (intradermally or subcutaneously).

In another embodiment, the disclosed nucleic acid GSK3β phosphorylation antagonists can be expressed within cells using vector systems with appropriate eukaryotic promoters.

i. Condensing Agents and Liposomes

In some embodiments, nucleic acid GSK3β phosphorylation antagonists can be combined with a condensing agent to form a nucleic acid delivery vehicle. Suitable polycations include, for example, polylysine, polyarginine, polyornithine, protamine, spermine, spermidine, and putrescine. Many suitable methods for making linkages between condensing agents and nucleic acids are known in the art.

In other embodiments, nucleic acid GSK3β phosphorylation antagonists can be associated with a liposome to form a nucleic acid delivery vehicle. Liposomes are small, lipid vesicles comprised of an aqueous compartment enclosed by a lipid bilayer, typically spherical or slightly elongated structures several hundred angstroms in diameter. Under appropriate conditions, a liposome can fuse with the plasma membrane of a cell or with the membrane of an endocytic vesicle within a cell that has internalized the liposome, thereby releasing its contents into the cytoplasm. Prior to interaction with the surface of a cell, however, the liposome membrane acts as a relatively impermeable barrier that sequesters and protects its contents, for example, from degradative enzymes. Additionally, because a liposome is a synthetic structure, specially designed liposomes can be produced that incorporate desirable features (Szoka, et al., *Biochim. Biophys. Acta*, 600:1-18 (1980); Bayer, et al., *Biochim. Biophys. Acta*. 550: 464-73 (1979); Rivnay, et al., *Meth. Enzymol*. 149:119-123 (1987); Wang, et al., *Proc. Natl. Acad. Sci. U.S.A*. 84: 7851-5 (1987); Plant, et al., *Anal. Biochem*. 176:420-6 (1989)).

Liposomal preparations include cationic (positively charged), anionic (negatively charged) and neutral preparations. Cationic liposomes have been shown to mediate intracellular delivery of plasmid DNA (Feigner, et al., *Proc. Natl. Acad. Sci. USA*, 84:7413-7416 (1987)), mRNA (Malone, et al., *Proc. Natl. Acad. Sci. USA*, 86:6077-6081 (1989)), and purified transcription factors (Debs, et al, *J. Biol. Chem.*, 265:10189- 10192 (1990), in functional form. Cationic liposomes are readily available. For example, N[1 -2,3 -dioleyloxy)propyl]-N,N,N-triethylammonium (DOTMA) liposomes are available under the trademark Lipofectin™, (GIBCO BRL, Grand Island, N.Y.), Transfectace (DDAB/DOPE) and DOTAP/DOPE (Boerhinger). Other cationic liposomes can be prepared from readily available materials using techniques available in the art.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE)e. These materials can also be mixed with the DOTMA and DOTAP starting materials in appropriate ratios. Methods for making liposomes using these materials are well known in the art.

The liposomes can comprise multilamellar vesicles (MLVs), small unilamellar vesicles (SUVs), or large unilamellar vesicles (LUVs). The various liposome-nucleic acid complexes are prepared using methods known in the art.

In addition, lipoproteins can be included with a nucleic acid for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of nucleic acids to cells expressing lipoprotein receptors. In some embodiments, if lipoproteins are included with a nucleic acid, no other targeting ligand is included in the composition. Receptor-mediated targeted delivery of nucleic acid GSK3β phosphorylation antagonists to specific tissues can also be used.

ii. Vectors

In another embodiment, nucleic acid GSK3β phosphorylation antagonists can be expressed from transcription units within cells using eukaryotic promoters in appropriate DNA/RNA vectors. Suitable vectors include, but are not limited to, DNA plasmids and viral vectors. GSK3β phosphorylation antagonist-expressing viral vectors can be constructed based on, but not limited to, adeno-associated virus, retrovirus, adenovirus, lentivirus, or alphavirus. In another embodiment, poi III based constructs are used to express nucleic acid molecules of the invention (U.S. Pat. Nos. 5,902,880 and 6,146,886). Viral vectors capable of producing either persistent or transient expression of nucleic acid GSK3β phosphorylation antagonists in cells can be used.

C. Kits

The formulations may be provided as a kit or other container. The kit or container holds an effective amount of a GSK3β phosphorylation antagonist as defined herein. In some embodiments the composition is provided as part of a bandage. For example, the compositions can be applied to one side of a bandage or a transdermal patch, or the bandage or patch can be saturated with a liquid suspension of the composition.

Liquid compositions containing GSK3β phosphorylation antagonists can be administered from absorbent materials, such as a bandage, patch or sponge, or as a spray or aerosol (applied to the affected area using a pump-type or aerosol sprayer). The use of a patch or bandage, into which the composition has been incorporated, is advantageous in that it the composition will be slowly and continuously released. Providing the composition in the form of a solution, which may initially be provided in a concentrated liquid form, or as a sterile dissolvable powder, for example, in a packet or syringe, requiring the addition of water, saline or other suitable diluents prior to use may be advantageous.

Solid compositions can be applied by any number of means, including the use of applicators or by patient self-administration. For example, creams, lotions, foams, pastes, ointments, or gels may be administered using an applicator, such as a squeeze-type or plunger-type applicator. Administering the composition as a cream having low surface tension is advantageous as it provides a uniform wetting action that assists in composition penetration into crypts and crevices of the wound. Such a creamy composition can also act as a moisturizer.

II. Methods of Use

A. Promotion of Epithelialization and Wound Healing

The GSK3β phosphorylation antagonists can be used to promote wound healing in chronic non-healing wounds. The examples demonstrate a general role for GSK3β phosphorylation in regulation of re-epithelialization of wounds. Specifically, the examples demonstrate that GSK3β becomes phosphorylated and subsequently degraded in the epidermis of chronic wounds. The examples also demonstrate that GSK3β becomes phosphorylated and degraded in keratinocytes exposed to GCs through the signaling pathways shown in FIG. 1, including through activation of PLC and PKC. Finally, the examples demonstrate that inhibitors of these signaling pathways that inhibit GSK3β phosphorylation, such as PKC inhibitors, can rescue GC-mediated inhibition of epithelialization. Therefore, GSK3β phosphorylation antagonists that inhibit or reduce the activation of these signaling pathways will be effective to promote wound healing in many epithelial tissues, including skin, mouth tissue, gingiva and corneal epithelium.

Wound healing involves a complex interaction between epidermal and dermal cells, the extracellular matrix, controlled angiogenesis, and plasma derived proteins, all coordinated by an array of cytokines and growth factors. This dynamic process has been classically divided into several overlapping phases: inflammation, proliferation, migration and remodeling.

The combination of new tissue and contraction of surrounding tissues is essential for the healing of chronic skin ulcers (Clark, *Dermatol. Clin.*, 11:657-666 (1993)). Fibroblasts are the key cells involved in the production of new extracellular matrix (in addition to producing collagen they produce tenascin, fibronectin, and proteoglycans such as hyaluronic acid). While this new matrix is synthesized, existing matrix in and around the wound region is degraded by several enzyme systems, including matrix metalloproteinases and plasminogen activators. The effect of metalloproteinases is regulated by tissue inhibitors, which are believed to be important in healing by preventing excessive matrix degradation (March, et al., *Arch. Dermatol, Res.*, 287:107-114 (1994)). At an injury site, keratinocytes are also a part of the primary response to injury, releasing a signal and mobilizing other cell types (macrophages, platelets, endothelial cells and fibroblasts) to the site of injury. In addition, keratinocytes respond to cellular signals by undergoing two processes: migration and proliferation. Both of these processes are important for complete epithelialization and wound closure. During healing, some keratinocytes at the wound edge proliferate. Others undergo a marked transformation to enable them to phagocytose debris and migrate across the wound bed. Keratinocyte migration, coupled with wound contraction, results in re-epithelialization and wound closure. However, the epidermal morphology of chronic wounds differs from the morphology of normal epidermis and suggests that keratinocytes do not successfully complete activation or differentiation in chronic wounds (Stojadinovic, et al., *Am. J. Pathol.*, 167:59-69 (2005); Morasso, et al., *Biol. Cell*, 97:173-183 (2005)). Instead, keratinocytes are caught in a "loop" of trying, but not succeeding, to accomplish either of the two processes. Keratinocytes at the non-healing edge of chronic wounds appear to be hyperproliferative but non-migratory, suggesting that lack of migration leads to inability to epithelialize and plays an important role in pathogenesis of chronic ulcers.

Methods for using the GSK3β phosphorylation antagonists to inhibit or reduce GSK3β phosphorylation and degradation in keratinocytes of non-healing wounds and to promote wound healing are provided. In one embodiment, the GSK3β phosphorylation antagonists are administered to an individual in an effective amount to inhibit or reduce GSK3β phosphorylation in chronic non-healing wounds. In another embodiment, the GSK3β phosphorylation antagonists are administered to an individual in an effective amount to inhibit or reduce induction of c-myc and nuclear presence of β-catenin in epidermal cells at the leading edge of chronic, non-healing wounds. In another embodiment, the GSK3β phosphorylation antagonists are administered to an individual in an effective amount to promote wound healing. As used herein, the phrases "promote wound healing" or "promote wound closure" refer to increasing keratinocyte migration in a wound, reducing the amount of time required for a wound to close, increasing the extent to which a wound closes, or a combination thereof.

GSK3β phosphorylation antagonists may be administered in any combination. For example, one or more GSK3β phosphorylation antagonists that target the same signaling molecule upstream of GSK3β may be co-administered. Alternatively, one or more GSK3β phosphorylation antagonists that target different signaling molecules upstream of GSK3β may be co-administered.

In one embodiment, the wound that is treated is a chronic non-healing wound. Representative chronic non-healing wounds that can be treated include, but are not limited to, diabetic ulcers, arterial ulcers, venous ulcers, pressure (decubitus) ulcers and burns.

In another embodiment, the wound that is treated using the disclosed GSK3β phosphorylation antagonists is an acute wound, such as a wound caused by acute injury or surgery.

B. Methods of Administration

The disclosed GSK3β phosphorylation antagonists can be administered topically or subcutaneously at or adjacent to the site of a wound. In a preferred embodiment, the GSK3β phosphorylation antagonists are administered topically. Topical administration may be in any suitable form, such as liquids, ointments, lotions, creams, gels, drops, sprays, patches or powders, as described above. The GSK3β phosphorylation antagonists may also be incorporated into inserts, wound dressings, or other materials that come into contact with the wound.

The GSK3β phosphorylation antagonists may for formulated into sustained release formulations such as polymeric delivery systems, mini-pumps, and hydrogels, as described above. These can be loaded with GSK3β phosphorylation antagonists, injected or implanted into the ulcers, where the GSK3β phosphorylation antagonists are released over a therapeutically effective time period.

The GSK3β phosphorylation antagonists may be administered in a single dose, in multiple doses, in a continuous or intermittent manner, depending, for example, upon the recipient's physiological condition. Administration of the compositions may be essentially continuous over an indeterminate period of time, for example, at regular intervals. Alternatively, the compositions can be administered continuously for a pre-selected period of time or in a series of spaced doses.

1. Effective Amounts

Effective dosages can be determined by extrapolation based on animal studies, for example, using a mouse model.

The C57BL/KsJ db/db mouse is a particularly useful model since it has been shown to be a clinically relevant model of impaired wound healing. The animals exhibit several characteristics of adult onset diabetes, including obesity, insulin-resistant hyperglycemia and markedly delayed wound closure. C57BL/KsJ-db/db mice, homozygous for the diabetes spontaneous mutation, become identifiably obese around 3 to 4 weeks of age. Elevations of plasma insulin begin at 10 to 14 days and of blood sugar at 4 to 8 weeks. Homozygous mutant mice are polyphagic, polydipsic, and polyuric. The course of the disease is markedly influenced by genetic background. A number of features are observed on the C57BLIKsJ db/db background, including an uncontrolled rise in blood sugar, severe depletion of the insulin-producing beta-cells of the pancreatic islets, and death by 10 months of age. Exogenous insulin fails to control blood glucose levels and gluconeogenic enzyme activity increases. The diabetic mutation is a result of a point mutation in the leptin receptor gene, lepr. This point mutation promotes abnormal splicing creating a stop codon that shortens the intracellular domain of the receptor, so that its signaling capacity is curtailed. The ligand, Leptin, has been shown to be a key weight control hormone that takes a mutant form in the mouse obesity mutation, Lepob (JAX Mice database: http://jaxmice.jax.org/jaxmic-e-cgi/jaxmicedb.cgi).

C57BL/KsJ-db/dbmice exhibit characteristics similar to those of human adult onset diabetes (NIDDM Type 11) as a result of a single autosomal recessive mutation on chromosome 4. Only the homozygous animals develop diabetes. This strain also expresses lower levels of several growth factors and receptors, accounting, at least in part, for the reduced rate of healing (Werner, et al., *J Invest Dermatol*, 103:469-473 (1994)).

The streptozotocin diabetic mouse is another model for studying the pathology of diabetes. Mice are rendered diabetic by intraperitoneal injection of streptozotocin administered for five consecutive days. Streptozotocin-treated mice become hyperglycemic and also show impaired wound healing when compared to healthy animals (Matsuda, et al. *J Exp Med*, 187:297-306 (1998); Brown, et al., *Am J Pathol*, 151: 715-724 (1997)). The streptozotocin-induced diabetic mouse has been widely studied and is known to those of skill in the art.

The diabetic mouse model (Geerlings, et al., *FEMS Immunol Med Microbial.*, 3-4:259-265 (1999); Feige, et al., *EXS.*, 77:359-373 (1996); Bessman, *J Diabetes Complications*, 4:258-262 (1992); Loots, et al., *J Invest Dermatol.*, 5:850-857 (1998); Brown, et al., *J Surg Research*, 56:562-570 (1994); Greenhalgh, et al., *Am J Pathol*, 136:1235-1246 (1990); Tsuboi, et al., *J Explorer Med*, 172:245-251 (1990); Matuxzewska, et al., *Pharm Res*, 11:65-71 (1994); Darby, et al., *Int J Biochem Cell Biol*, 29:191-200 (1997); Livant, et al., *J Clin Invest.*, 105:1537-1545 (2000); Yamamota, et al., *Europ J Pharm*, 302:53-60 (1996); Wetzler, et al., *J Invest Dermatol.*, 115:245-253 (2000); Sun, et al., *J Invest Dermatol*, 108:313-318 (1997); Sun, et al., *J Invest Dermatol.*, 106:232-237 (1996); Zykova, et al., *Diabetes*, 49:1461-1458 (2002); Beer, et al., *J Invest Dermatol.*, 109: 132-138 (1997)) has been widely accepted in the study of therapeutic agents that may be effective in the treatment of chronic wounds, it has been successfully used in preclinical testing for growth factor therapies, and it offers a good model for patients with diabetic foot ulcers and other chronic, non-healing wounds.

C. Combination Therapies

Other therapeutic agents, for example, anti-microbial agents, pain relievers, anti-inflammatory agents, growth factors (e.g., PDGF), vitamins (e.g., vitamin B, C or E), aloe Vera or similar materials, may also be administered.

For example, GSK3β phosphorylation antagonists can also be applied in combination with other skin treatments such as an exfolliant or laser treatment. Likewise, GSK3β phosphorylation antagonists can also be applied in combination with one or more of classes of antibiotics, including, but not limited to, Aminoglycosides, Cephalosporins, Chloramphenicol, Clindamycin, Erythromycins, Fluoroquinolones, Macrolides, Azolides, Metronidazole, Penicillins, Tetracyclines, Trimethoprim-sulfamethoxazole, or Vancomycin.

GSK3β phosphorylation antagonists can also be applied in combination with one or more of classes of steroids, including, but not limited to, Andranes (e.g., Testosterone), Cholestanes (e.g., Cholesterol), Cholic acids (e.g., Cholic acid), Corticosteroids (e.g., Dexamethasone), Estraenes (e.g., Estradiol), or Pregnanes (e.g., Progesterone).

GSK3β phosphorylation antagonists can also be applied in combination with one or more of classes of narcotic and non-narcotic analgesics, including, but not limited to, Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, or Pentazocine.

GSK3β phosphorylation antagonists can also be applied in combination with one or more of classes of anti-inflammatory agents, including, but not limited to, Alclofenac, Alclometasone Dipropionate, Algestone Acetonide, alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Decanoate, Deflazacort, Delatestryl, Depo-Testosterone, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lomoxicam, Loteprednol Etabonate, Meclofenamate Sodium, Meclofenamic Acid, Meclorisone Dibutyrate, Mefenamic Acid, Mesalamine, Meseclazone, Mesterolone, Methandrostenolone, Methenolone, Methenolone Acetate, Methylprednisolone Suleptanate, Momiflumate, Nabumetone, Nandrolone, Naproxen, Naproxen Sodium, Naproxol, Nimazone, Olsalazine Sodium, Orgotein, Orpanoxin, Oxandrolane, Oxaprozin, Oxyphenbutazone, Oxymetholone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Sanguinarium Chloride, Seclazone, Sermetacin, Stanozolol, Sudoxicam, Sulindac, Suprofen, Talmetacin, Talniflurnate, Talosalate, Tebufelone, Tenidap, Tenidap Sodium, Tenoxicam, Tesicam, Tesimide, Testosterone, Testosterone Blends, Tetrydamine, Tiopinac, Tixocortol Pivalate, Tolmetin, Tolmetin Sodium, Triflumidate, Zidometacin, or Zomepirac Sodium.

GSK3β phosphorylation antagonists can also be applied in combination with one or more of classes of anti-histaminic agents, including, but not limited to, Ethanolamines (e.g., diphenhydrmine carbinoxamine), Ethylenediamine (e.g., tripelennamine pyrilamine), Alkylamine (e.g., chlorpheniramine, dexchlorpheniramine, brompheniramine, triprolidine), astemizole, loratadine, fexofenadine, Brompheniramine, Clemastine, Acetaminophen, Pseudoephedrine, or Triprolidine.

The GSK3β phosphorylation antagonists can also be applied in combination with other strategies for promoting healing of chronic wounds. For example, negative pressure therapy is currently being used to promote healing of chronic wounds. These and other therapies can be combined with the disclosed GSK3β phosphorylation antagonists for improved results.

EXAMPLES

Example 1

Activation of c-myc by Glucocorticoids (GCs) Contributes to Inhibition of Epithelialization Materials and Methods:
Microarray Analysis Microarray Suite 5.0 (Affymetrix) was used for data extraction and for further analysis, data mining tool 3.0 (Affymetrix, Santa Clara, Calif.) and GeneSpring™ software 7.3.1 (Silicon Genetics, Redwood City, Calif.) were used for normalization to the median and filtration on the Volcano plot for degree of change and p-value calculations. Samples were normalized per chip: to the $50^{th}$ percentile and per gene to a median. Statistical comparisons of expression level between each condition were performed using ANOVA test. Only genes with a p-value less than 0.05 were considered to be statistically significant. Differential expressions of transcripts were determined by calculating the degree of change. Genes were considered regulated if the expression levels differed more than 2-fold relative to healthy skin. Clustering was performed based on individual gene expression profiles. An extensive gene annotation table was developed, describing the molecular function and biological category of the genes present on the chip as previously described (Stojadinovic, Jour. Biol. Chem. (2007); Stojadinovic, et al., JCMM (2008); Brem, et al., Mol. Med. 2008)). The genes were annotated according to this table (Lee, Methods Mol. Biol. 2010; 585:193-223 (2009)).

Northern Blotting

RNA isolation and purification was performed using Triazol (Invitrogen, Carlsbad, CA) extraction and subsequently Qiagen RNeasy kit column purification (Qiagen, Valencia, Calif.) followed by Northern blot as described (Radoja, Mol. Cell. Biol., 20:4328-4339 (2000)). c-myc and GAPDH probes were generated as described (Li, et al., FASEB J., 15:2533-2535 (2001)). Densitometry tracing of the films was performed using GS-800 calibrating densitometer (Bio-Rad, Hercules, Calif.) and the image was quantified using Quantity One 4.1.1 program (Bio-Rad). The values were normalized to the loading control (GAPDH) for each condition.

Immunohistochemistry

Samples were fixed in formalin and routinely processed for paraffin embedding. Paraffin-embedded tissue was sectioned and 5-μm-thick sections. Keratinocytes were grown on chamber slides to 70% continency (Lab-Tek, Naperville, Ill.) and treated with 0.1 μmol/L dexamethasone (Sigma). Cells were fixed in 70% methanol for 10 minutes and permeabilized with 0.1% Triton X-100 for 10 minutes. For staining human tissues and cultured cells a c-myc antibody (Santa Cruz Biotechnology, Santa Cruz, Calif.) was used at 1:100 dilution at 4° C. using the Vectastain ABC kit (Vector Laboratories, Burlingame, Calif.) following commercial protocol. The slides were analyzed using a Nikon microscope and digital images were obtained using a Spot RTcolor camera.

Results:

Using comparative microarray analyses it was found that c-myc mRNA is induced by glucocorticoids (GCs) whereas it is repressed in early phases of wound healing, which was confirmed using Northern blot analyses. It was also found that the protein level of c-myc was induced by topical GCs as detected by prominent nuclear staining compared to the control (untreated) skin. This indicates that c-myc is repressed initially in epithelialization, and by the activation of a stop signal (GCs), its expression is shifted from repressed to induced. Targeted overexpression of c-myc in basal keratinocytes leads to impairment of keratinocyte migration and consequently inhibition of wound healing in a transgenic mouse model (Waikel, et al., Nat. Genet., 28:165-8 (2001)). Therefore, GC-mediated induction of c-myc directly correlates with the finding that GCs inhibit keratinocyte migration. Immunohistochemistry demonstrated that c-myc is induced in keratinocytes at the non-healing edge in patients with chronic wounds, suggesting that it contributes to inhibition of keratinocyte migration. These studies identify c-myc as a target gene in keratinocytes at the leading edge of non-healing wounds that plays an important role in the inhibition of epithelialization.

Example 2

GCs Stabilize Nuclear β-catenin Leading to the Inhibition of Keratinocyte Migration and Epithelialization Materials and Methods:
Immunohistochemistry Topical GC treatment of human skin cepsimens was performed by daily applica-tion of Cormax (Clobetasol Propionate Cream 0.05%; Oclassen Pharmaceuticals, Inc.) using a sterile Q-tip applicator. Samples were fixed in formalin and processed for paraffin embedding following by sectioning to obtain 5-μm-thick sections. Keratinocytes were grown on chamber slides to 70% confluency (Lab-Tek, Naperville, Ill.) and treated with 0.1 μmol/L dexamethasone (Sigma) and incubated in the presence or absence of 200 nM Calphostin C or 10 μM RU486. Cells were fixed in 70% methanol for 10 minutes and permeabilized with 0.1% Triton X-100 for 10 minutes. Human tissues were stained with β-catenin antibody β-catenin phosphorylated Ab (Tyr- 142) (AbCam) at 1:1500 dilution in 5% bovine serum albumin and visualized using a secondary fluorescein isothiocyanate anti-mouse IgG antibody 1:150 (Sigma). All sections were mounted with mounting media. All negative controls were prepared by substitution of the primary antibody with an irrelevant antibody. The sections were analyzed using a Carl Zeiss microscope (Carl Zeiss, Thornwood, N.Y.) and digital images were collected using Adobe TWAIN_32 program.

Migration Assay

Primary human keratinocytes were grown to 80% confluency. Twenty-four hours before the experiment cells were transferred to basal KBM medium (Life Technologies, Inc., Grand Island, N.Y.). Before the scratch, cells were treated with 8 μg/ml mitomycin C (ICN, Irvine, Calif.) for 1 hour and washed with basal media. Scratches were performed as previously described (Lee, et al., J Mol. Biol., 345:1083-1097 (2005)). Cells were incubated with 20 μmol/L LiCl or 25 ng/ml of EGF for 24 and 48 hours, rephotographed, and cell migration was quantified as previously described (Lee, et al., J. Mol. Biol., 345:1083-1097 (2005); Zavadil. et al., EMBO J., 23:1155-1165 (2004)). Thirty measurements were taken for each experimental condition and distance coverage by cells moving into the scratch wound area was quantified. Three images were analyzed per condition, per time point, and averages and standard deviations were calculated.

Human Skin ex vivo Wound Model

Wounds were created using 4-mm punch biopsies through the reticular dermis and a rim of cells participating in wound healing was collected by re-punching around the initial wounded area. Each time point was collected in parallel with an unwounded skin specimen of the same donor. All specimens were collected and either stored in RNAlater (Ambion, Austin, Tex.) or frozen in OCT compound (Tissue Tek, Reading, Calif.) for immunocytochemistry. To activate β-catenin, wounded skin was maintained on the air-liquid interface in the presence or absence of 20 mmol/L LiCl (Shimm, et al., J. Biol. Chem., 278:19674-19681 (2003)). Wounds were quantified by planimetry as described previously (Stojadinovic, et al., Am. J. Pathol., 167(1):59-69 (2005)).

Results:

c-myc is a downstream target of the Wnt/β-catenin signaling pathway. To establish the role of β-catenin in c-myc activation by GCs, the regulation of its expression by GCs was tested. No changes were found in either mRNA or protein levels of P-catenin in keratinocytes treated with GCs. An alternative possibility is that GCs may regulate stabilization of β-catenin rather than its transcription. To test that hypothesis, skin was treated with topical GCs which resulted in robust nuclear localization of β-catenin in epidermis of treated skin, whereas in untreated skin, β-catenin was found on the membrane and not in nuclei. This was confirmed in primary human epidermal keratinocytes (HEK) cultures using β-catenin specific antibody that recognizes only phosphorylated form (β-catenin y142). GC-mediated nuclearization of β-catenin was blocked by the protein kinase C (PKC) inhibitor, Calphostin C, indicating that PKC may be involved in activation. As expected, the GC antagonist, RU486, also blocked activation of β-catenin. If GCs activate β-catenin and, as a consequence, c-myc is induced and keratinocyte migration is inhibited, it is possible that the activation of β-catenin might lead to inhibition of keratinocyte migration and to inhibition of epithelialization. Using the wound scratch assay, it was found that LiCl, by stabilizing β-catenin, inhibited keratinocyte migration while EGF promoted it (Stojadinovic, et at, *Am. J. Pathol.*, 167:59-69 (2005)). Moreover, LiCl efficiently blocked EGF-stimulated keratinocyte migration. This dominant inhibitory effect of β-catenin has important clinical implications because numerous proinflammatory cytokines and growth factors are released at the site of the wound and failure of keratinocytes to respond appropriately to these stimuli may contribute to chronic wound formation. Therefore, β-catenin contributes to the development of a chronic wound by inhibiting keratinocyte migration both directly by activating c-myc, and indirectly by blocking the effects of other growth factors and cytokines. If this is true, one may expect that, by activating β-catenin, an acute wound may be "converted" to a chronic wound. To test this, healthy skin was wounded by a 4 mm biopsy punch and maintained at the air-liquid interface in the presence or absence of LiCl. Wound healing was measured 4 days later. This time point was specifically chosen because healing is in its exponential phase and keratinocyte migration should be actively progressing at this point. The healing rate was measured by planimetry and evaluated by histology (Stojadinovic, et al., *Am. J. Pathol.*, 167:59-69 (2005)). Indeed, stabilization of nuclear β-catenin completely inhibited wound healing, thus converting an acute wound into a chronic wound phenotype. This further implicates the role of GCs in inhibition of wound healing because they not only activates catenin but also inhibit keratinocyte migration and, through interaction with β-catenin, GCs suppress K6 expression.

Example 3

GC-Activated (β-catenin Induces LEF/TCF-Mediated Transcription Through PKC Activity Materials and Methods:
Primary human keratinocytes were plated into 6-well plates and grown to 70% confluence in defined serum-free keratinocyte medium supplemented with epidermal growth factor and bovine pituitary extract (keratinocyte-SFM, GIBCO). Prior to transfection cells were transferred to basal serum—free medium (GIBCO) for 6 h, and then transfected with Tcf/Lef transcriptional activation reporter construct SuperTopFlash (Masckauchán, *Mol. Biol. Cell*, 17(12):5163-5172 (2006)) containing Tcf responsive elements and *renilla*-luciferase construct. Transfections were performed in triplicates using 3 μg of reporter plasmid, 0.2 μg of *renilla*-luciferase plasmid with a FuGene 6 transfection reagent (Roche), following manufacturer's instructions for procedure. Cells were incubated at 37° C. for over night with transfection cocktail and than treated with Dexamethasone (1 μM), RU486 (10 μM) and Calphostine C (200 nM) for 24 hours. Cell lysates were prepared the next day and both firefly and renilla luciferase activities were evaluated using Dual-Luciferase Reporter Assay System (Promega, Madison, Wis.). Samples were read in a luminometer and values were normalized for transfection efficiency using renilla-luciferase activity.

Figure 2A:
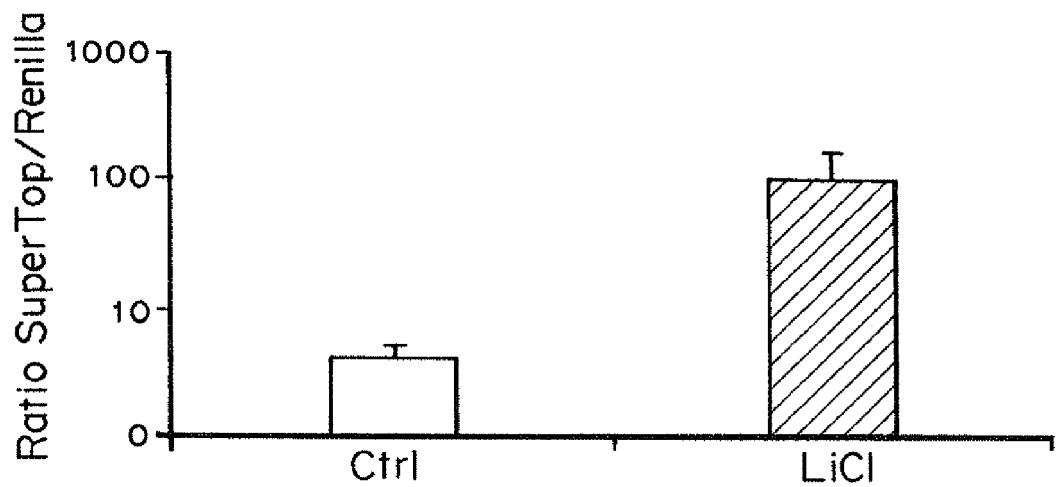
FIG. 2A is a bar graph showing activation of lymphoid enhancer factor/T-cell factor (LEF/TCF)-mediate transcription in the absence or presence of LiCl. Activation of LEF/TCF-mediated transcription by LiCl was used as a positive control for activation by the glucocorticoid dexamethasone in FIG. 2B. Activation of LEF/TCF-mediated transcription was measured using a Super-TOP-flash luciferase reporter vector containing TCF-responsive promoter elements. Renilla luciferase activity was used as an internal control. Data are expressed as a ratio of Super-TOP-flash luciferase activity to Renilla luciferase activity.
Figure 2B:
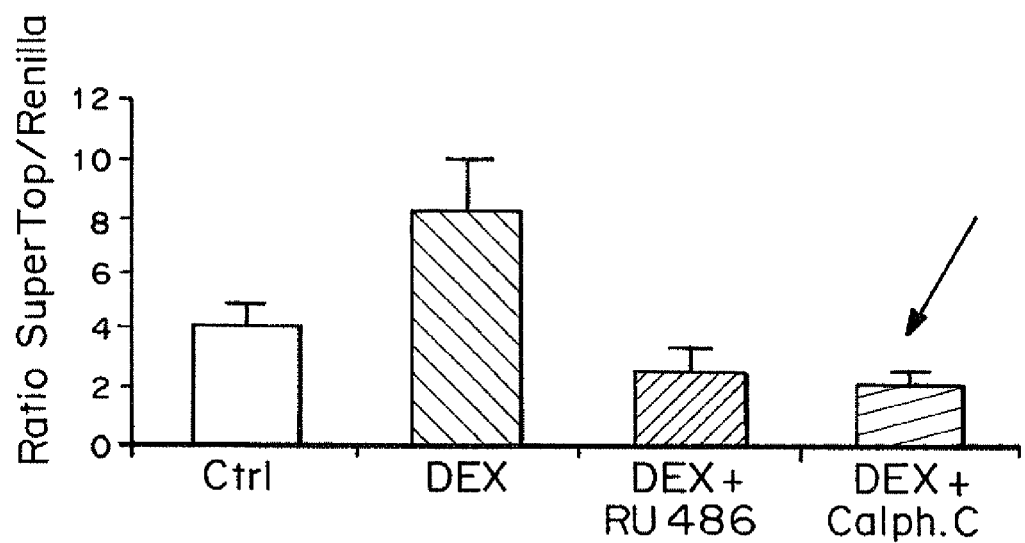
FIG. 2B is a bar graph showing activation of LEF/TCF-mediated transcription by dexamethasone, in the absence or presence of the glucocorticoid receptor (GR) antagonist, RU486, or the protein kinase C (PKC) inhibitor, calphostin C. Activation of LEF/TCF-mediated transcription was measured using a Super-TOP-flash luciferase reporter vector containing TCF-responsive promoter elements. Renilla luciferase activity was used as an internal control. Data are expressed as a ratio of Super-TOP-flash luciferase activity to Renilla luciferase activity.

Results:
To test if GCs induce LEF/TCF-mediated transcriptional regulation though activation of β-catenin primary human epidermal keratinocytes were co-transfected with Tcf/Lef transcriptional activation reporter construct SuperTopFlash (Masckauchan, et al., *Mol. Biol. Cell*, 17:5163-72 (2006)) containing Tcf responsive elements. Cells were treated with GCs and subjected to luciferase assays. Cells treated with LiCl served as a positive control and, as expected, showed increase activity of TopFlash (FIG. 2A). It was found that GCs induced LEF/TCF-mediated transcription (FIG. 2B). To test if this induction was indeed GCs-mediated a known GCs inhibitor, RU486 (Zhang, et al., *Steroids*, 72:600-8 (2007)) was used, which abolished dexamethasone-mediated induction (FIG. 2B). To further test the mechanism through which GCs-mediated activation of β-catenin occurs LEF/TCF transcriptional regulation was measured in the presence of Calphostin C, a PKC inhibitor in co-transfection experiments. It was found that. GCs-mediated induction of LEF/TCF activity was blocked in the presence of the PKC inhibitor (FIG. 2B). This suggests that GCs-mediated phosphorylation of GSK3β and nuclearization of β-catenin occurs via PKC.

Example 4

GC-mediated c-myc Activation is PKC-Dependent.

Materials and Methods:
Western blot
Extracts for immunoblotting were prepared from a subconfluent 100 mm plate of normal HEK treated with DEX (1 μM), Calphostine C and RU486 (10 μM) or an equal volume of ethanol vehicle 4 hours prior to lysis. Cells were placed on ice; washed twice with phosphate-buffer saline (PBS); and lysed in 0.5 ml of modified RIPA buffer containing 50 mM Hepes, pH 7.5, 150 mM NaCl, 1 mM EDTA, 1 mM EGTA, 1 mM NaF, 1% Triton X-100, 10% glycerol, and additional protease and phosphatase inhibitors (1 mM phenylmethylsulfonyl fluoride, 20 mM glycerophosphate, 8 mM sodium pyrophosphate, 1 μg/ml leupeptin, 1 μg/ml pepstatin A, and 1 μg/ml aprotinin (Roche, Indianapolis, Ind.)) through fine needle aspiration. Lysates were centrifuged at 13,000 rpm for 10 min at 4° C. The soluble supernatants were normalized for total protein concentration using the Bradford protein assay, and the samples were stored at −20° C. Cell extracts were boiled for 5 minutes in Leammli sample buffer, were separated by 10% SDS-PAGE and transferred to nitrocellulose membrane (VWR, Batavia, Ill.) on 100 V for 1 hour in Tris/glycine transfer buffer. The membranes were blocked for 30 minutes in 5% bovine serum albumin in blocking solution (Tris-buffered saline (TBS, pH 7.4) at room temperature and then incubated in blocking solution with primary antibody at 4° C. overnight using 1:500 of serum for anti-c-myc antibody (Santa Cruz). The membranes were washed three times for 5 minutes with TBS and 0.1% Triton X-100 and twice with TBS and incubated for 1 hour at room temperature with horseradish peroxidase-conjugated secondary antibody (Santa Cruz, Calif.). Blots were then washed three times for 5 minutes with TBS and 0.1% Triton X-100 and developed using Super Signal West Pico Chemiluminescent substrate (Pierce, Rockford, Ill.) and exposed on x-ray film (Eastman Kodak Co. Bio Max MR-Film) according to the manufacturer's instructions. For loading control we used anti b-tubulin antibody (Santa Cruz, Santa Cruz, Calif.). Western blot quantification was done using Total Lab Program (Non-linear dynamics Inc., NC).

Results:

The examples above demonstrate that GCs mediate activation of c-myc on both mRNA and protein levels. Furthermore, it has been shown that c-myc is over-expressed in patients with chronic wounds. In addition, β-catenin signaling is also activated in epidermis of patients with chronic wounds and GCs mediate activation of β-catenin via GSK3β phosphorylation. It was postulated that this phosphorylation is PKC-dependent. To determine if c-myc activation by GCs occurs via PKC activation HEK cells were treated with GCs in the presence of the PKC inhibitor Calphostin C and c-myc induction was measured using Western blot. It was found that GCs induce c-myc 4 hours after treatment with GCs and further, Calphostin C blocked this activation, indicating that the induction of c-myc by GCs is mediated through PKC. In addition, the GCs antagonist RU486 was used as a control. As expected, RU486 also blocked GCs-mediated c-myc activation.

Example 5

GCs Mediate GSKV Phosphorylation and Degradation through PKC Pathway

Materials and Methods:
Western Blot

Details of the protocol are explained in Example 4. Keratinocytes were treated with DEX (1 µM), GO6979 (400 µM) or RU486 (10 µM) or equal volume of ethanol vehicle 4 h prior to lysis. The membranes were incubated in blocking solution with primary antibody at 4° C. overnight using 1:500 of anti-phospho-GSK3b (ser 9) antibody (Cell Signalling). For loading control 1:12000 anti GAPDH polyclonal antibody (Santa Cruz, Santa Cruz, Calif.) was used.

Results:

To determine the mechanism through which GCs caused activation of β-catenin pathway, the Wnt pathway regulator molecule, GSK3β, was investigated. Inhibition of GSK3β is known to prevent degradation of cytoplasmic β-catenin, thus allowing its nuclearization and transcriptional activity. It was found that GCs treatment suppress GSK3β at both the mRNA and protein levels. GSK3β is known to be phosphorylated on Ser 9, which consequentially leads to its inactivation. Therefore, it was hypothesized that GCs promote phosphorylation of GSK3β, thus leading to its inactivation. To test this, a specific antibody that recognizes only the phosphorylated form of GSK3β (Ser 9) was used, leading to the finding that GCs indeed promote GSK3β phosphorylation. This effect was most prominent at 30-45 minutes post treatment whereas by 24 hours, degradation of GSK3 β becomes evident. To test if this phosphorylation is mediated through GR, the receptor inhibitor, RU486, was used. Dexamethasone-mediated phosphorylation of GSK3β was completely abolished by RU486. To further determine the mechanism through which GCs mediate GSK3β phosphorylation, the GO6967 inhibitor, which blocks classical PKC (α, β and γ), was used. RU486 was used as a control. It was found that both GO6967 and RU486 block dexamethasone-mediated phosphorylation of GSK3β.

Example 6

GCs Mediate GSK3β Phosphorylation and Degradation through PLC-ePKC Pathway

Materials and Methods:
Western blot

Details of the protocol are explained under Example 4. Keratinocytes were treated with DEX (1 µM), U73122 (10 µM) or equal volume of ethanol vehicle 4 hours prior to lysis. The membranes were incubated in blocking solution with primary antibody at 4° C. overnight using 1:500 of anti-phospho-GSK3b (ser 9) antibody (Cell Signalling). For loading control 1:12000 anti GAPDH polyclonal antibody (Santa Cruz, Santa Cruz, Calif.) was used.

Results:

To further establish the mechanism of dexamethasone-mediated GSK3β phosphorylation, U73122, an inhibitor of phospholipase C (PLC), was used. It was found that U73122 inhibits dexamethasone-mediated GSK3β phosphorylation. This suggests that GSK3β phosphorylation occurs through activation of PLC that, in turn, activates cPKCs through diacylglycerol (DAG), inositol triphosphate ($IP_3$) and $Ca^{2+}$.

Example 7

GSK3β Degradation is Found in Patients with Chronic Wounds

Materials and Methods:
Immunohistochemistry

Chronic wounds were obtained from biopsies of consenting patients having surgical debridement. Specimens were fixed in 4% paraformaldehyde overnight (Sigma—Aldrich) at room temperature, dehydrated with ethanol, and embedded in paraffin. 5 µm thick tissue sections were serially cut on a microtome (HM 315, Carl Zeiss) and mounted on slides. Sections were de-waxed in xylene, re-hydrated and washed with 1XPBS. For antigen retrieval, paraffin sections were heated in 95° C. water bath in Target Retrieval Solution (DAKO Corporation). Histological slides were treated with 0.1% $H_2O_2$ in Methanol for 30 minutes, rinsed with $H_2O$, and blocked with normal rabbit serum for 30 minutes (Vectastain Kit Elite ABC, Vector Labs). Sections were then incubated with anti-phospho-Ser211 (GR-P) antibody (1:250) in a commercially available antibody diluent (DAKO Antibody Diluent with Background Reducing Components, DAKO Corporation) for one hour at room temperature. A rabbit biotinylated secondary antibody was added and avidin-biotin complex was visualized using DAB (Vectorlabs, DAB Peroxidase Substrate Kit). Slides were counterstained with hematoxylin. As a negative control, 1× PBS was substituted for primary antibody. Sections were analyzed using a Carl Zeiss microscope. Digital images were taken with the Adobe TWAIN_32 program.

Western Blot

Human skin specimens were obtained from reduction mammoplasty in accordance to approved institutional protocol and used to generate acute wounds as previously described (Tomic-Canic, et al., *Wound Repair Regen.*, 15(1): 71-9 (2007)). A 3 mm biopsy punch was used to create an acute wound and skin specimens were maintained at the air-liquid interface with DMEM (BioWhittaker), antibiotic/antimycotic and fetal bovine serum (FBS) (Gemimi Bio-Products) for 0, 4, 24, 48, and 96 hours. Chronic wounds were obtained from biopsies of consenting patients having surgical debridement as described above. Protein extraction and Western blot was performed as detailed in Example 4. The membranes were incubated in blocking solution with primary antibody at 4° C. overnight using 1:500 of anti-phospho-GSK3b (ser 9) antibody (Cell Signaling).

Results:

Biopsies obtained from patients with chronic wounds were investigated. To test if GCs-mediated suppression of GSK3β participates in inhibition of epithelialization in chronic wounds, through β-cateninlc-myc signaling, biopsies from patients suffering from chronic wounds were obtained and the level of GSK3β was evaluated. A decrease of GSK3β protein levels in non-healing edge biopsies from patients with chronic wounds (impaired epithelialization) was found. Analyses of the epidermis of these biopsies revealed the activation of hormone-activated GR. This means that GSK3β down regulation correlates with activation of GR pathway and furthermore with keratinocyte phenotype demonstrating inhibition of epithelialization.

Example 8

Topical Application of the PKC Inhibitor, Calphostin C, Rescues GC-mediated Inhibition of Epithelialization Materials and Methods:
Human Skin Wound Model Wounds were created using 4-mm punch biopsies through the reticular dermis and incubated on the air-liquid interface, as previously described. Immediately upon wounding cells were treated topically with dexamethasone (DEX) (1 μM), Calphostine C (CC) (200 μM) and the combination, DEX+CC and maintained on the air-liquid interface for 6 days. All specimens were frozen in OCT compound (Tissue Tek, Reading; Calif.) for immunocytochemistry. Wounds were quantified by planimetry as described previously (Tomic-Canic, et al., *Wound Repair Regen.*, 15(1):71-9 (2007)).

Results:

The Examples above demonstrate that GC-mediated non-genomic effects on keratinocytes involve a PKC-dependent signaling mechanism. To test the involvement of PKC in a tissue model, wounds were treated with the PKC inhibitor, calphostin C, in the presence or absence of dexamethasone. The results demonstrated that calphostin C rescues dexamethasone-mediated inhibition of epithelialization. This indicates that calphostin C blocks effects of endogenously synthesized GC.

Overall, the data presented in the examples indicates a model in which inhibition of epithelialization participates in the chronic wound development. Keratinocytes at the wound edge become targeted by sustained activation of GR. This further leads to phosphorylation and degradation of GSK3β, activating β-catenin and c-myc and also causing cytoskeletal changes. Together, these changes lead to the inhibition of keratinocyte migration and de-regulation of their growth and differentiation.

Unless defined otherwise, all technical and scientific terms used herein have the same meanings as commonly understood by one of skill in the art to which the disclosed invention belongs.

Those skilled in the art will recognize, or be able to ascertain using no more than routine experimentation, many equivalents to the specific embodiments of the invention described herein. Such equivalents are intended to be encompassed by the following claims.

We claim:

1. A method for promoting wound healing comprising, administering to a subject in need thereof a pharmaceutical composition comprising an antagonist of GSK3β serine phosphorylation in an effective amount to promote epithelialization of the wound to promote healing of the wound
wherein the antagonist of glycogen synthase kinase 3 beta (GSK3β) serine phosphorylation does not directly inhibit protein kinase C (PKC), and wherein the wound is a chronic wound.

2. The method of claim 1, wherein the pharmaceutical composition comprises an antagonist of GSK3β serine phosphorylation in an effective amount to promote proliferation and migration of keratinocytes at the leading edge of the chronic wound.

3. The method of claim 1, wherein the pharmaceutical composition comprises an antagonist of GSK3β serine phosphorylation in an effective amount to inhibit or reduce nuclearization of β-catenin and induction of c-myc in keratinocytes contacted with a glucocorticoid.

4. The method of claim 1, wherein the antagonist of GSK3β serine phosphorylation comprises a small molecule or peptide that inhibits or reduces the enzymatic activity, or enzymatic product, of an upstream molecule activated by glucocorticoids in the GSK3β signaling pathway, thereby inhibiting or reducing phosphorylation of GSK3β on serine 9.

5. The method of claim 4, wherein the upstream molecule activated by glucocorticoids in the GSK3β signaling pathway is selected from the group consisting of phospholipase C (PLC), G alpha q (Gαq), protein tyrosine kinases (PTK), and the glucocorticoid receptor (GR).

6. The method of claim 5, wherein the antagonist of GSK3β phosphorylation is the PLC inhibitor U-73122.

7. The method of claim 5, wherein the antagonist of GSK3β phosphorylation is the PTK inhibitor genistein.

8. The method of claim 5, wherein the antagonist of GSK3β phosphorylation is the Gaq inhibitor YM-254890.

9. The method of claim 5, wherein the antagonist of GSK3β phosphorylation is the GR inhibitor RU-486.

10. The method of claim 5, wherein the antagonist of GSK3β phosphorylation is the inositol triphosphate ($IP_3$) receptor inhibitor 2-Aminoethoxydiphenyl borate (2-APB), xestospongin C, or 8-(N,N-Diethylamino)-octyl-3,4,5-trimethoxybenzoate (TMB-8).

11. The method of claim 1, wherein the wound is in a tissue selected from the group consisting of skin, mouth tissue, gingiva, and corneal epithelium.

12. The method of claim 1, wherein the chronic wound is selected from the group consisting of diabetic ulcers, arterial ulcers, venous ulcers, pressure ulcers, mouth ulcers, sickle cell ulcers, corticosteroid-induced wounds and burns.

13. The method of claim 12, wherein the diabetic ulcer is a diabetic foot ulcer.

14. The method of claim 1, wherein the wound is a skin wound.

15. The method of claim 14, wherein the pharmaceutical composition promotes keratinocyte epithelialization.

16. The method of claim 14, wherein the pharmaceutical composition is formulated for topical delivery.

17. The method of claim 16, wherein the pharmaceutical composition is a liquid, spray, aerosol, ointment, foam, cream, gel, paste, powder/talc or solid.

18. A method for promoting healing of a chronic wound comprising administering to a subject in need thereof a pharmaceutical composition comprising a single active agent, wherein the active agent consists of a Protein Kinase C (PKC) inhibitor in an effective amount to promote epithelialization of the chronic wound to promote healing of the wound.

19. The method of claim 18, wherein the PKC inhibitor is calphostin C or Go 6976.

* * * * *